(12) United States Patent
Laping

(10) Patent No.: US 6,309,856 B1
(45) Date of Patent: Oct. 30, 2001

(54) HUMAN MAD PROTEINS AND USES THEREOF

(75) Inventor: Nicholas J. Laping, West Chester, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/183,228

(22) Filed: Oct. 30, 1998

Related U.S. Application Data

(62) Division of application No. 08/732,028, filed on Oct. 16, 1996, now Pat. No. 5,866,693.

(51) Int. Cl.$^7$ ................................................ C12N 15/00
(52) U.S. Cl. ...................... 435/69.1; 530/350; 536/23.1; 536/23.5
(58) Field of Search ........................... 530/350; 536/23.1, 536/23.5; 435/69.1

(56) References Cited

FOREIGN PATENT DOCUMENTS

WO95/14772    6/1995  (WO).

OTHER PUBLICATIONS

Burgess et al J Cell Biol vol. 111 2129–2138, 1990.*
Lazar et al Mol Cell Biol vol. 8(3):1247–1252, Mar. 1988.*
Acland et al Nature vol. 343:662–665, 1990.*
Zhang et al Nature vol. 383:168–172, 1996.*
Kurokawa et al., "The oncoprotein Evi–1 represses TGF–β signalling by inhibiting Smad3," Nature, vol. 394, No. 6688, pp. 92–96 (1998).
Imamura et al., "Smad6 inhibits signalling by the TGF–β superfamily," Nature, vol. 389, No. 6651, pp. 622–626 (1997).
Nakao et al., "Identification of Smad7, a TGFβ–inducilble antagonist of TGF–α signalling," Nature, vol. 389, No. 6651, pp. 631–635 (1997).
Tsukazaki et al., "SARA, a FYVE Domain Protein that Recruits Smad2 to the TGFβ Receptor," Cell, vol. 95, No. 6, pp. 779–791 (1998).
Baer et al., "Transforming growth factor betas and their receptors in human liver cirrhosis," European Jour. of Gastroenterology and Hepatology, vol. 10, No. 12, pp. 1031–1039 (1998).
Ward et al., "Vascular types I and II transforming growth factor-beta receptor expression: differential dependency on tyrosine kinases during induction by TGF–β," FEBS Lett., pp. 197–200 (1998).
Chen et al., "Suppression of transforming growth factor–β–induced apoptosis through a phosphatidylinositol 3–kinase/Akt–dependent pathway," Oncogene, vol. 17, No. 15, pp. 1959–1968 (1998).
Stockwell et al., "TGF–62 –signaling with small molecule FKBP12 antagonists that bind myristoylated FKBP12–TGF–β type 1 receptor fusion proteins," Chem. & Bio., vol. 5, No. 7, pp. 385–395 (1998).
Goumans et al., "Mouse embryonic stem cells with aberrant transforming growth factor β signalling exhibit impaired differentiation in vitro and in vivo," Differentiation, vol. 63, No. 3, pp. 101–113 (1998).
Ward et al., "Inhibitory effects of tranilast on expression of transforming growth factor–β isoforms and receptors in injured arteries," Atherosclerosis, vol. 137, No. 2, pp. 267–275 (1998).
Goto et al., "a single missense mutant of Smad3 inhibits activation of both Smad2 and Smad3, and has a dominant negative effect on TGF–β signals," FEBS Lett., vol. 430, No. 3, pp. 201–204 (1998).
Shen et al., "TGF–β–induced Phosphorylation of Smad3 Regulates Its Interation with Coactivator p300/CREB–binding Protein," Molecular Biology of the Cell, vol. 9, No. 12, pp. 3309–3319 (1998).
Ali et al, "Angiotensin–Converting Enzyme Inhibition Attentuates Proteinuria and Renal TGF–β1 mRNA Expression in Rats with Chronic Renal Disease," Pharmacology, vol. 57, No. 1, pp. 20–27 (1998).
Coppa et al., "Restored Expression of Transforming Growth Factor β Type II Receptor in k–ras–Transformed Thyroid Cells, TGFβ–Resistant, Reverts Their Malignant Phenotype," Journal of Cellular Physiology, vol. 172, No. 2, pp. 200–208 (1997).
Sekelsky et al., Genetics, vol. 139, pp. 1347–1358. (3/95).
Sulston et al., Nature, vol. 356, pp. 37–41. (3/92).
Wilson et al., Nature, vol. 368, pp. 32–38. (3/94).
Howard et al., Cell, vol. 71, pp. 637–647 (11/92).
Reeck et al., Cell, vol. 50, pp. 667 (8/87).
Lewin et al., Science, vol. 237, pp. 1570 (1987).
Eppert et al., "MADR2 Maps to 18q21 and Encodes a TGFβ–Regulated MAD–Related Protein that is Functionally Mutated in Colorectal Carcinoma", Cell, vol. 86, pp. 543–552 (1996).
GenBank Accession No. U68018, Zhang, et al., Jul. 2, 1999 (Rel. 60, Last updated, Version 4).

\* cited by examiner

Primary Examiner—Sheela Huff
Assistant Examiner—Larry R. Helms
(74) Attorney, Agent, or Firm—William T. Han; Ratner & Prestia; William T. King

(57) ABSTRACT

Human MADr3 or MADr4 polypeptides and DNA (RNA) encoding such MADr3 or MADr4 and a procedure for producing such polypeptides by recombinant techniques is disclosed. Also disclosed are methods for utilizing such MADr3 or MADr4, or compounds which inhibit or stimulate MADr3 or MADr4 for stimulating wound healing, and treating cancers, among others, are also disclosed. Agonist and antagonists of these MAD proteins and methods of their use are also disclosed. Also disclosed are diagnostic assays for detecting diseases related to mutations in the nucleic acid sequences and altered concentrations of the polypeptides. Also disclosed are diagnostic assays for detecting mutations in the polynucleotides encoding the MADr3 or MADr4 and for detecting altered levels of the polypeptide in a host.

3 Claims, 6 Drawing Sheets

FIGURE 1A

```
GGCACGAGGT CGAGCCCAGC CCCGCCGGGG GCGCTCCTCG CCGCCCGCGC                    50

GCCCTCCCCA GCC ATG TCG TCC ATC CTG CCT TTC ACT CCC CCG ATC               96
            Met Ser Ser Ile Leu Pro Phe Thr Pro Pro Ile
             1           5                       10

GTG AAG CGC CTG CTG GGC TGG AAG AAG GGC GAG CAG AAC GGG CAG              141
Val Lys Arg Leu Leu Gly Trp Lys Lys Gly Glu Gln Asn Gly Gln
         15              20                  25

GAG GAG AAA TGG TGC GAG AAG GCG GTC AAG AGC CTG GTC AAG AAA              186
Glu Glu Lys Trp Cys Glu Lys Ala Val Lys Ser Leu Val Lys Lys
         30              35                  40

CTC AAG AAG ACG GGG CAG CTG GAC GAG CTG GAG AAG GCC ATC ACC              231
Leu Lys Lys Thr Gly Gln Leu Asp Glu Leu Glu Lys Ala Ile Thr
         45              50                  55

ACG CAG AAC GCC AAC ACC AAG TGC ATC ACC ATC CCC AGG TCC CTG              276
Thr Gln Asn Ala Asn Thr Lys Cys Ile Thr Ile Pro Arg Ser Leu
         60              65                  70

GAT GGC CGG TTG CAG GTG TCC CAT CGG AAG GGG CTC CCT CAT GTC              321
Asp Gly Arg Leu Gln Val Ser His Arg Lys Gly Leu Pro His Val
         75              80                  85

ATC TAC TGC CGC CTG TGG CGA TGG CCA GAC CTG CAC AGC CAC CAC              366
Ile Tyr Cys Arg Leu Trp Arg Trp Pro Asp Leu His Ser His His
         90              95                 100

GAG CTG CGG GCC ATG GAG CTG TGT GAG TTC GCC TTC AAT ATG AAG              411
Glu Leu Arg Ala Met Glu Leu Cys Glu Phe Ala Phe Asn Met Lys
        105             110                 115

AAG GAC GAG GTC TGC GTG AAT CCC TAC CAC TAC CAG AGA GTA GAG              456
Lys Asp Glu Val Cys Val Asn Pro Tyr His Tyr Gln Arg Val Glu
        120             125                 130

ACA CCA GTT CTA CCT CCT GTG TTG GTG CCA CGC CAC ACA GAG ATC              501
Thr Pro Val Leu Pro Pro Val Leu Val Pro Arg His Thr Glu Ile
        135             140                 145

CCG GCC GAG TTC CCC CCA CTG GAC GAC TAC AGC CAT TCC ATC CCC              546
Pro Ala Glu Phe Pro Pro Leu Asp Asp Tyr Ser His Ser Ile Pro
        150             155                 160

GAA AAC ACT AAC TTC CCC GCA GGC ATC GAG CCC CAG AGC AAT ATT              591
Glu Asn Thr Asn Phe Pro Ala Gly Ile Glu Pro Gln Ser Asn Ile
        165             170                 175
```

FIGURE 1B

| | | | | | | | | | | | | | |
|---|---|---|---|---|---|---|---|---|---|---|---|---|---|
| CCA | GAG | ACC | CCA | CCC | CCT | GGC | TAC | CTG | AGT | GAA | GAT | GGA | GAA ACC | 636 |
| Pro | Glu | Thr | Pro 180 | Pro | Pro | Gly | Tyr | Leu 185 | Ser | Glu | Asp | Gly | Glu Thr 190 |

```
CCA GAG ACC CCA CCC CCT GGC TAC CTG AGT GAA GAT GGA GAA ACC    636
Pro Glu Thr Pro Pro Pro Gly Tyr Leu Ser Glu Asp Gly Glu Thr
            180             185                     190

AGT GAC CAC CAG ATG AAC CAC AGC ATG GAC GCA GGT TCT CCA AAC    681
Ser Asp His Gln Met Asn His Ser Met Asp Ala Gly Ser Pro Asn
            195             200                     205

CTA TCC CCG AAT CCG ATG TCC CCA GCA CAT AAT AAC TTG GAC CTG    726
Leu Ser Pro Asn Pro Met Ser Pro Ala His Asn Asn Leu Asp Leu
            210             215                     220

CAG CCA GTT ACC TAC TGC GAG CCG GCC TTC TGG TGC TCC ATC TCC    771
Gln Pro Val Thr Tyr Cys Glu Pro Ala Phe Trp Cys Ser Ile Ser
            225             230                     235

TAC TAC GAG CTG AAC CAG CGC GTC GGG GAG ACA TTC CAC GCC TCG    816
Tyr Tyr Glu Leu Asn Gln Arg Val Gly Glu Thr Phe His Ala Ser
            240             245                     250

CAG CCA TCC ATG ACT GTG GAT GGC TTC ACC GAC CCC TCC AAT TCG    861
Gln Pro Ser Met Thr Val Asp Gly Phe Thr Asp Pro Ser Asn Ser
            255             260                     265

GAG CGC TTC TGC CTA GGG CTG CTC TCC AAT GTC AAC AGG AAT GCA    906
Glu Arg Phe Cys Leu Gly Leu Leu Ser Asn Val Asn Arg Asn Ala
            270             275                     280

GCA GTG GAG CTG ACA CGG AGA CAC ATC GGA AGA GGC GTG CGG CTC    951
Ala Val Glu Leu Thr Arg Arg His Ile Gly Arg Gly Val Arg Leu
            285             290                     295

TAC TAC ATC GGA GGG GAG GTC TTC GCA GAG TGC CTC AGT GAC AGC    996
Tyr Tyr Ile Gly Gly Glu Val Phe Ala Glu Cys Leu Ser Asp Ser
            300             305                     310

GCT ATT TTT GTC CAG TCT CCC AAC TGT AAC CAG CGC TAT GGC TGG    1041
Ala Ile Phe Val Gln Ser Pro Asn Cys Asn Gln Arg Tyr Gly Trp
            315             320                     325

CAC CCG GCC ACC GTC TGC AAG ATC CCA CCA GGA TGC AAC CTG AAG    1086
His Pro Ala Thr Val Cys Lys Ile Pro Pro Gly Cys Asn Leu Lys
            330             335                     340

ATC TTC AAC AAC CAG GAG TTC GCT GCC CTC CTG GCC CAG TCG GTC    1131
Ile Phe Asn Asn Gln Glu Phe Ala Ala Leu Leu Ala Gln Ser Val
            345             350                     355
```

FIGURE 1C

```
AAC CAG GGC TTT GAG GCT GTC TAC CAG TTG ACC CGA ATG TGC ACC    1176
Asn Gln Gly Phe Glu Ala Val Tyr Gln Leu Thr Arg Met Cys Thr
            360                 365                 370

ATC CGC ATG AGC TTC GTC AAA GGC TGG GGA GCG GAG TAC AGG AGA    1221
Ile Arg Met Ser Phe Val Lys Gly Trp Gly Ala Glu Tyr Arg Arg
            375                 380                 385

CAG ACT GTG ACC AGT ACC CCC TGC TGG ATT GAG CTG CAC CTG AAT    1266
Gln Thr Val Thr Ser Thr Pro Cys Trp Ile Glu Leu His Leu Asn
            390                 395                 400

GGG CCT TTG CAG TGG CTT GAC AAG GTC CTC ACC CAG ATG GGC TCC    1311
Gly Pro Leu Gln Trp Leu Asp Lys Val Leu Thr Gln Met Gly Ser
            405                 410                 415

CCA AGC ATC CGC TGT TCC AGT GTG TCT TAGAGACATC AAGTATGGTA      1358
Pro Ser Ile Arg Cys Ser Ser Val Ser
            420                 425

GGGGAGGGCA GGCTTGGGGA AAATGGCCAT GCAGGAGGTG GAGAAAATTG         1408

GAACTCTACT CAACCCATTG TTGTCAAGGA AGAAGAAATC TTTCTCCCTC         1458

AACTGAAGGG GTGCACCCAC CTGTTTTCTG AAACACACGA GCAAACCCAG         1508

AGGTGGATGT TATGAACAGC TGTGTCTGCC AAACACATTT ACCCTTTGGC         1558

CCCACTTTGA AGGGCAAGAA ATGGCGTCTG CTCTGGTGGC TTAAGTGAGC         1608

AGAACAGGTA GTATTACACC ACCGGCCCCC TCCCCCCAGA TCTTTTTTTG         1658

AGTGACAGCT TTCTGGGATG TCACAGTCCA ACCAGAAACA CCCCTCTGTC         1708

TAGGACTGCA GTGTGGAGTT CACCTTGGAA GGGCGTTCTA GGTAGGAAGA         1758

GCCCGCAGGG CCATGCAGAC CTCATGCCCA GCTCTCTGAC GCTTGTGACA         1808

GTGCCTCTTC CAGTGAACAT TCCAGCCCA GCCCGCCCC GCCCCGCCCC           1858

ACCACTCCAG CAGACCTTGC CCCTTGTGAG CTGGATAGAC TTGGGATGGG         1908

GAGGGAGGGA GTTTTGTCTG TCTCCCTCCC CTCTCAGAAC ATACTGATTG         1958

GGAGGTGCGT GTTCAGCAGA ACCTGCACAC AGGACAGCGG GAAAAATCGA         2008

TGAGCGCCAC CTCTTTAAAA ACTCACTTAC GTTTGTCCTT TTTCACTTTG         2058

AAAAGTTGGA AGGATCTGCT GAGGCCCAGT GCATATGCAA TGTATAGTGT         2108
```

FIGURE 1D

| | | | | |
|---|---|---|---|---|
| CTATTATCAC | ATTAATCTCA | AAGAGATTCG | AATGACGGTA | AGTGTTCTCA | 2158
| TGAAGCAGGA | GGCCCTTGTC | GTGGGATGGC | ATTTGGTCTC | AGGCAGCACC | 2208
| ACACTGGGTG | CGTCTCCAGT | CATCTGTAAG | AGCTTGCTCC | AGATTCTGAT | 2258
| GCATACGGCT | ATATTGGTTT | ATGTAGTCAG | TTGCATTCAT | TAAATCAACT | 2308
| TTATCATAAA | AAAAAAAAAA | AAAAA | | | 2333

FIGURE 2

```
CTGGCTCAGT CTNTTAATCA GGGTNTTGAA GCAGTCTATC ANCTAACTAG      50

AATGGGGGGG ATAAGTTTTT TGTTTNGTGA AAGGGTGNGG AGCAGTATAC     100

CGAAGTCAGT ACGNTAACAN NAGACTNCTA ACTGGATTGA ACTTCATNTG     150

AATGGACCTC TACANTGGNT GGACAAAGTA TTAACTCAGA TNGGATACCC     200

TNCAGTGCGT TGCTCAAGNA TGTCATAAAG CTTCACCAAT CAAGTCCCAT     250

GAAAAGACT TAAANGTAAC AACTCTN                              277
```

FIGURE 3

```
TGACATACTG CATGCCTGAG TGAGAGACGA TCCGAACTCT GTGCTAGTCA        50

TCTGCAGCAC ACTAACTATT ATGCTGATGT GACTCATTGC AGTTTAAACA       100

TTTCTTCTGT TTGCATCTCT AGTAGAAATG GAAATAACC ACTCCCTGGC        150

GCTCTTTTCA TTAAATTTTC ATATTTTGA AAAAAAAA                     189
```

HUMAN MAD PROTEINS AND USES THEREOF

This application is a division of application Ser. No. 08/732,028, filed Oct. 16, 1996, now U.S. Pat. No. 5,866,693, whose entire contents are herein incorporated by reference in their entirety.

FIELD OF THE INVENTION

This invention relates to newly identified polynucleotides, polypeptides encoded by such polynucleotides, the use of such polynucleotides and polypeptides, as well as the production of such polynucleotides and polypeptides. The polypeptides of the present invention has been putatively identified as human MAD homologs. More particularly, one polypeptide of the present invention has been putatively identified as a novel human MAD protein, sometimes hereafter referred to as "MADr3". The invention also relates to inhibiting or stimulating the actions of such polypeptides.

BACKGROUND OF THE INVENTION

Cellular growth and differentiation appear to be initiated, promoted, maintained and regulated by a multiplicity of stimulatory, inhibitory and synergistic factors and hormones. The alteration and/or breakdown of the cellular homeostasis mechanism seems to be a fundamental cause of growth related diseases. Growth modular factors are implicated in a wide variety of pathological and physiological processes including signal transduction, cell communication, growth and development, embryogenesis, immune response, hematopoiesis cell survival and differentiation, inflammation, tissue repair and remodeling, atherosclerosis and cancer.

The transforming growth factor β (TGF-β) family of cytokines/growth factors regulates cell proliferation, differentiation, recognition and death, and figures in the control of development, tissue recycling and repair. Included in this family are Drosophila decapentaplegic (DPP) [Sekelsky et al, *Proc. Natl. Acad. Sci., USA*, 139:1347–1358 (1995)], TGFβ-1, TGFβ-2 and TGFβ-3; and bone morphogenetic proteins, BMP2/BMP4 [Hoodless et al, *Cell*, 85:489–500 (1996); Graff et al, *Cell*, 85:479–487 (1996); Liu et al, *Nature*, 381:620–623 (1996); and Vhang et al, *Nature*, 383:168–1782 (1996)].

TGF-β family members signal by simultaneously contacting two transmembrane serine/threonine kinases known as the type I and type II receptors. Certain proteins mediate the complex signalling cascade of the TGF-β family. It has been suggested that different TGF-β family members may signal through different MAD isoforms. MAD (Mothers against DPP) protein was discovered in Drosophila to be required for the signal transduction of DPP. Other MAD proteins in other species, such as Xenopus, mouse, and human, have been found to transduce signaling of BMP2/BMP4.

Several reports suggest that subsequent to ligand activation, the TGF-β type I receptor phosphorylates MAD [Hoodless et al, cited above; and Liu et al, cited above]. The phosphorylated MAD then translocates into the nucleus and effects gene expression of selected early intermediate genes specific to the MAD isoform subtype [J. Massague, *Cell*, 85:947–950 (June 28, 1996)].

Therefore, selective antagonists of the MAD isoforms are anticipated to be beneficial in many diseases where selective interruption of TGF-β or BMP signaling are indicated [see, e.g., Eppert et al, *Cell*, 86:543–552 (Aug. 23, 1996)]. Such disorders include, without limitation, chronic renal failure, scarring, colorectal carcinoma, and cardiovascular disease.

There, thus, exists a need in the art for a variety of TGF-β signalling proteins, antagonists and agonists thereof, as well as compositions and methods for the use of same.

SUMMARY OF THE INVENTION

In one aspect, the present invention provides polypeptides, inter alia, that have been identified as novel MAD polypeptides of human origin, as well as biologically active and diagnostically or therapeutically useful fragments, variants, analogs and derivatives thereof, variants and derivatives of the fragments, and analogs of the foregoing. In one embodiment, the polypeptide is human MADr3. In another embodiment, the polypeptide is human MADr4. These polypeptides have been identified as MAD polypeptides, e.g., by homology between the amino acid sequence or nucleotide sequence of known MAD polypeptides.

Among the particularly preferred embodiments of this aspect of the invention are variants of human MADr3 and MADr4 encoded by naturally occurring alleles of the human genes for same.

In another aspect of the present invention, there are provided non-naturally occurring synthetic, isolated and/or recombinant MADr3 or MADr4 polypeptides, fragments, consensus fragments and/or sequences having conservative amino acid substitutions of the MADr3 or MADr4 of the present invention. These polypeptides may bind MADr3 or MADr4 ligands, or may also modulate, quantitatively or qualitatively, MADr3 or MADr4 ligand binding.

In another aspect, the present invention provides synthetic, isolated or recombinant polypeptides which are designed to inhibit or mimic various MADr3 or MADr4 or fragments thereof.

In another aspect of the invention, there are provided isolated nucleic acid molecules encoding MAD polypeptides, particularly human MADr3 and MADr4. Such molecules include polynucleotides, mRNAs, DNAs, cDNAs, genomic DNAs and fragments thereof, as well as analogs and biologically active and diagnostically or therapeutically useful variants, analogs or derivatives thereof, including fragments of the variants, analogs and derivatives.

In a particularly preferred embodiment of this aspect of the invention, the polynucleotide comprises the region encoding human MADr3 in the sequence set out in FIGS. 1A–1D [SEQ ID NOS: 1 and 2]. In another particularly preferred embodiment of this aspect of the invention, the polynucleotide comprises the region of human MADr4 in the sequence set out in FIGS. 2 and 3 [SEQ ID NOS: 3 and 4].

Among the particularly preferred embodiments of this aspect of the invention are naturally occurring allelic variants of human MADr3 and MADr4.

In yet another aspect of the present invention, there is provided an isolated nucleic acid molecule encoding a mature polypeptide expressible from the human cDNA contained in plasmid pHSBHI91.

In still another aspect, this invention provides nucleic acid probes comprising nucleic acid molecules of sufficient length to specifically hybridize to nucleic acid sequences of the present invention, e.g., human MADr3 or MADr4 sequences.

In another aspect, the invention provides a process for producing the aforementioned polypeptides, polypeptide fragments, variants and derivatives, fragments of the variants and derivatives, and analogs of the foregoing. In a preferred embodiment, the invention provides methods for producing the aforementioned MADr3 and MADr4 polypeptides by recombinant techniques comprising culturing recombinant prokaryotic and/or eukaryotic host cells, containing (i.e., having expressibly incorporated therein) a nucleic acid sequence encoding a polypeptide of the present invention under conditions for expression of human MAD polypeptide in the host and then recovering the expressed polypeptide.

In still another aspect, the invention provides products, compositions, processes and methods that utilize the aforementioned polypeptides and polynucleotides for research, biological, clinical and therapeutic purposes, inter alia. MAD polypeptides, particularly human MADr3 and MADr4 polypeptides, may be employed for therapeutic purposes, including, but not limited to, treatments to stimulate wound healing, to restore normal neurological functioning after trauma or AIDS dementia, to treat ocular disorders, to target certain cells, to treat kidney and liver disorders, to prevent scarring; to treat ulcers and corneal incisions, and to treat cancers.

Also provided are compositions and methods that can be useful as potential modulators of MADr3 or MADr4 function, by binding to ligands or modulating ligand binding, due to their expected biological properties, which may be used in diagnostic, therapeutic and/or research applications.

In another aspect, the invention provides a method for utilizing these polypeptides and proteins for the screening of chemical or natural compounds or ligands thereof which inhibit or stimulate the phosphorylation of the MAD polypeptides, inhibit or stimulate their interaction with other proteins, inhibit or stimulate the translocation of these polypeptides to the nucleus, and inhibit or stimulate the interaction of these polypeptides with nucleic acid sequences.

In accordance with certain preferred embodiments of this aspect of the invention, there are provided products, compositions and methods, inter alia, for, among other things, assessing MADr3 or MADr4 expression in cells by determining MADr3 or MADr4 polypeptides or MADr3 or MADr4-encoding mRNA; treating dysfunctions or diseases including, but not limited to, those identified above, in vitro, ex vivo or in vivo by exposing cells to MADr3 or MADr4 polypeptides or polynucleotides as disclosed herein; assaying genetic variation and aberrations, such as defects, in MADr3 or MADr4 genes; and administering a MADr3 or MADr4 polypeptide or polynucleotide to an organism to augment MADr3 or MADr4 function or remediate MADr3 or MADr4 dysfunction.

In yet another aspect of the present invention, there is provided a process of using such activating compounds to stimulate the polypeptides of the present invention for the treatment of conditions related to the under-expression of MADr3 or MADr4.

In still a further aspect of the present invention, there is provided a process of using such inhibiting compounds for treating conditions associated with over-expression of MADr3 or MADr4.

In another aspect of the invention, there are provided antibodies against MAD polypeptides, including humanized antibodies, anti-antibodies, monoclonal and polyclonal antibodies. In certain particularly preferred embodiments in this regard, the antibodies are highly selective for human MADr3 or MADr4.

In yet a further aspect, the present invention provides agonists to the polypeptides of the present invention. Agonists to the polypeptides of the present invention can be used in the treatment of cancer, benign prostate hypertrophy, and wound healing. Among preferred agonists are molecules that mimic MADr3 or MADr4, that bind to MADr3 or MADr4-binding molecules or receptor molecules, and that elicit or augment MADr3 or MADr4-induced responses. Also among preferred agonists are molecules that interact with MADr3 or MADr4 or MADr3 or MADr4 polypeptides, or with other modulators of MADr3 or MADr4 activities, and thereby potentiate or augment an effect of MADr3 or MADr4 or more than one effect of MADr3 or MADr4.

In another aspect of the present invention, there are provided MADr3 or MADr4 antagonists, which can be targeted against the phosphorylation of MAD, translocation, modification of other downstream proteins, and interaction with cis elements. Antagonists of MADr3 activity can be used in the treatment of chronic renal failure, acute renal failure, wound healing and prevention of scar formation, arthritis, osteoporosis, atherosclerosis, polycystic kidney disease and congestive heart failure. Among preferred antagonists are those which mimic MADr3 or MADr4 so as to bind to MADr3 or MADr4 receptor or binding molecules but not elicit a MADr3 or MADr4-induced response or more than one MADr3 or MADr4-induced response. Also among preferred antagonists are molecules that bind to or interact with MADr3 or MADr4 so as to inhibit an effect of MADr3 or MADr4 or more than one effect of MADr3 or MADr4 or which prevent expression of MADr3 or MADr4. Also among preferred antagonists are molecules that bind kinases which phosphorylate MADr3 or MADr4, and thereby prevent phosphorylation of MADr3 and MADr4.

In a further aspect of the invention, there are provided compositions comprising a MADr3 or MADr4 polynucleotide or a MADr3 or MADr4 polypeptide for administration to cells in vitro, to cells ex vivo and to cells in vivo, or to a multicellular organism. In certain particularly preferred embodiments of this aspect of the invention, the compositions comprise a MADr3 or MADr4 polynucleotide for expression of a MADr3 or MADr4 polypeptide in a host organism for treatment of disease. Particularly preferred in this regard is expression in a human patient for treatment of a dysfunction associated with aberrant endogenous activity of MADr3 or MADr4.

In still another aspect, the present invention provides diagnostic assays for detecting diseases related to overexpression of the polypeptides of the present invention and mutations in the nucleic acid sequences encoding such polypeptide. For example, the sequence of MADr3 can be used in diagnostics for the detection of overexpression which would be useful in detection of bone disease, renal failure, cardiovascular disease, and cancers of the colon, breast brain, kidney and liver.

Another aspect of this invention provides a process for utilizing these sequences in the detection of mutations of these MAD polypeptides as indicators of cancer.

A further aspect of the present invention provides a process for utilizing such polypeptides, or polynucleotides encoding such polypeptides, for in vitro purposes related to scientific research, synthesis of DNA and manufacture of DNA vectors.

Other objects, features, advantages and aspects of the present invention will become apparent to those of skill in the art from the following description. It should be understood, however, that the following description and the specific examples, while indicating preferred embodiments of the invention, are given by way of illustration only.

Various changes and modifications within the spirit and scope of the disclosed invention will become readily apparent to those skilled in the art from reading the following description and from reading the other parts of the present disclosure.

BRIEF DESCRIPTION OF THE DRAWINGS

The following drawings depict certain embodiments of the invention. They are illustrative only and do not limit the invention otherwise disclosed herein.

FIGS. 1A through 1D report the continuous cDNA sequence [SEQ ID NO: 1] and corresponding deduced amino acid sequence [SEQ ID NO: 2] of MADr3. The standard one letter abbreviations for amino acids are used.

FIG. 2 depicts the cDNA sequence of a fragment [SEQ ID NO: 3] of a partial clone, referred to as MADr4.

FIG. 3 depicts the cDNA sequence of a fragment [SEQ ID NO: 4] of the partial clone, MADr4.

The following illustrative explanations are provided to facilitate understanding of certain terms used frequently herein, particularly in the examples. The explanations are provided as a convenience and are not meant to limit the invention.

The term "gene" means the segment of DNA involved in producing a polypeptide chain; it includes regions preceding and following the coding region (leader and trailer) as well as intervening sequences (introns) between individual coding segments (exons).

"Digestion" of DNA refers to catalytic cleavage of a DNA with an enzyme, such as, but not limited to, a restriction enzyme that acts only at certain sequences in the DNA. The various restriction enzymes referred to herein are commercially available and their reaction conditions, cofactors and other requirements for use are known and routine to the skilled artisan.

For analytical purposes, typically, 1 microgram of plasmid or DNA fragment is digested with about 2 units of enzyme in about 20 microliter of reaction buffer. For the purpose of isolating DNA fragments for plasmid construction, typically 5 to 50 micrograms of DNA are digested with 20 to 250 units of enzyme in proportionately larger volumes. Appropriate buffers and substrate amounts for particular restriction enzymes are described in standard laboratory manuals, such as those referenced below, and they are specified by commercial suppliers.

Incubation times of about 1 hour at 37° C. are ordinarily used, but conditions may vary in accordance with standard procedures, the supplier's instructions, and the particulars of the reaction. After digestion, reactions may be analyzed, and fragments may be purified by electrophoresis through an agarose or polyacrylamide gel, using well known methods that are routine for those skilled in the art to isolate the desired fragment.

"Genetic element" generally means a polynucleotide comprising a region that encodes a polypeptide or a region that regulates replication, transcription or translation or other processes important to expression of the polypeptide in a host cell, or a polynucleotide comprising both a region that encodes a polypeptide and a region operably linked thereto that regulates expression.

Genetic elements may be comprised within a vector that replicates as an episomal element; that is, as a molecule physically independent of the host cell genome. They may be comprised within mini-chromosomes, such as those that arise during amplification of transfected DNA by methotrexate selection in eukaryotic cells. Genetic elements also may be comprised within a host cell genome, not in their natural state but, rather, following manipulation such as isolation, cloning and introduction into a host cell in the form of purified DNA or in a vector, among others.

"Isolated" means altered "by the hand of man" from its natural state; i.e., that, if it occurs in nature, it has been changed or removed from its original environment, or both. For example, a naturally occurring polynucleotide or a polypeptide naturally present in a living animal in its natural state is not "isolated", but the same polynucleotide or polypeptide separated from the coexisting materials of its natural state is "isolated", as the term is employed herein. With respect to polynucleotides, the term "isolated" means that it is separated from the chromosome and cell in which it naturally occurs.

As part of or following isolation, such polynucleotides can be joined to other polynucleotides, such as DNAs, for mutagenesis, to form fusion proteins, and for propagation or expression in a host, for instance. The isolated polynucleotides, alone or joined to other polynucleotides such as vectors, can be introduced into host cells, in culture or in whole organisms. Introduced into host cells in culture or in whole organisms, such DNAs still would be isolated, because they would not be in their naturally occurring form or environment. Similarly, the polynucleotides and polypeptides may occur in a composition, such as a media, formulations, solutions for introduction of polynucleotides or polypeptides, for example, into cells, compositions or solutions for chemical or enzymatic reactions, for instance, which are not naturally occurring compositions, and, therein remain isolated polynucleotides or polypeptides within the meaning of that term as it is employed herein.

"Ligation" refers to the process of forming phosphodiester bonds between two or more polynucleotides, which most often are double stranded DNAs. Techniques for ligation are well known to the art and protocols for ligation are described in standard laboratory manuals and references, such as, for instance, Sambrook et al., MOLECULAR CLONING, A LABORATORY MANUAL, 2nd Ed.; Cold Spring Harbor Laboratory Press, Cold Spring Harbor, N.Y., 1989, hereinafter referred to as "Sambrook et al".

"Oligonucleotide(s)" refers to relatively short polynucleotides. Often the term refers to single-stranded deoxyribonucleotides, but it can refer as well to single-or double-stranded ribonucleotides, RNA:DNA hybrids and double-stranded DNAs, among others. Oligonucleotides, such as single-stranded DNA probe oligonucleotides, often are synthesized by chemical methods, such as those implemented on automated oligonucleotide synthesizers. However, oligonucleotides can be made by a variety of other methods, including in vitro recombinant DNA-mediated techniques and by expression of DNAs in cells and organisms.

Initially, chemically synthesized DNAs typically are obtained without a 5' phosphate. The 5' ends of such oligonucleotides are not substrates for phosphodiester bond formation by ligation reactions that employ DNA ligases typically used to form recombinant DNA molecules. Where ligation of such oligonucleotides is desired, a phosphate can be added by standard techniques, such as those that employ a kinase and ATP.

The 3' end of a chemically synthesized oligonucleotide generally has a free hydroxyl group and, in the presence of a ligase, such as T4 DNA ligase, will readily form a phosphodiester bond with a 5' phosphate of another polynucleotide, such as another oligonucleotide. As is well known, this reaction can be prevented selectively, where desired, by removing the 5' phosphates of the other polynucleotide(s) prior to ligation.

"Plasmids" are genetic elements that are stably inherited without being a part of the chromosome of their host cell. They may be comprised of DNA or RNA and may be linear or circular. Plasmids code for molecules that ensure their replication and stable inheritance during cell replication and may encode products of considerable medical, agricultural and environmental importance. For example, they code for toxins that greatly increase the virulence of pathogenic bacteria. They can also encode genes that confer resistance to antibiotics. Plasmids are widely used in molecular biology as vectors used to clone and express recombinant genes. Plasmids generally are designated herein by a lower case p preceded and/or followed by capital letters and/or numbers, in accordance with standard naming conventions that are familiar to those of skill in the art. Starting plasmids disclosed herein are either commercially available, publicly available, or can be constructed from available plasmids by routine application of well known, published procedures. Many plasmids and other cloning and expression vectors that can be used in accordance with the present invention are well known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

"Polynucleotide(s)" generally refers to any polyribonucleotide or polydeoxyribonucleotide, which may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is a mixture of single- and double-stranded regions, hybrid molecules comprising DNA and RNA that may be single-stranded or, more typically, double-stranded or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are polynucleotides as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide, as it is employed herein, embraces such chemically, enzymatically or metabolically modified forms of polynucleotides, as well as the chemical forms of DNA and RNA characteristic of viruses and cells, including inter alia simple and complex cells.

"Polypeptides", as used herein, includes all polypeptides as described below. The basic structure of polypeptides is well known and has been described in innumerable textbooks and other publications in the art. The term is used herein to refer to any peptide or protein comprising two or more amino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins, of which there are many types.

It will be appreciated that polypeptides often contain amino acids other than the 20 amino acids commonly referred to as the 20 naturally occurring amino acids, and that many amino acids, including the terminal amino acids, may be modified in a given polypeptide, either by natural processes, such as processing and other post-translational modifications, or by chemical modification techniques which are well known to the art. The. numerous common modifications that occur naturally in polypeptides are well described in basic texts and in more detailed monographs, as well as in a voluminous research literature, and are well known to those of skill in the art.

Among the known modifications which may be present in polypeptides of the present invention are, without limitation, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, PROTEINS—STRUCTURE AND MOLECULAR PROPERTIES, 2nd Ed., T. E. Creighton, W. H. Freeman and Company, New York, 1993. Many detailed reviews are available on this subject, such as those provided by Wold, F., "Posttranslational Protein Modifications: Perspectives and Prospects", pgs. 1–12 in POSTTRANSLATIONAL COVALENT MODIFICATION OF PROTEINS, B. C. Johnson, Ed., Academic Press, New York, 1983; Seifter et al., *Meth. Enzymol.*, 182:626–646 (1990), and Rattan et al., *Ann. N.Y. Acad. Sci.*, 663:48–62 (1992).

It will be appreciated, as is well known and as noted above, that polypeptides are not always entirely linear. For instance, polypeptides may be branched as a result of ubiquitination, and they may be circular, with or without branching, generally as a result of posttranslational events, including natural processing event and events brought about by human manipulation which do not occur naturally. Circular, branched and branched circular polypeptides may be synthesized by non-translation natural processes and by entirely synthetic methods, as well.

Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention. For instance, the amino terminal residue of polypeptides made in E. coli, prior to processing, almost invariably will be N-formylmethionine.

The modifications that occur in a polypeptide often will be a function of how it is made. For polypeptides made by expressing a cloned gene in a host, for instance, the nature and extent of the modifications in large part will be determined by the host cell's posttranslational modification capacity and the modification signals present in the polypeptide amino acid sequence. For instance, as is well known, glycosylation often does not occur in bacterial hosts such as E. coli. Accordingly, when glycosylation is desired, a polypeptide should be expressed in a glycosylating host, generally a eukaryotic cell. Insect cells often carry out the same posttranslational glycosylations as mammalian cells and, for this reason, insect cell expression systems have been developed to express efficiently mammalian proteins having the native patterns of glycosylation, inter alia. Similar considerations apply to other modifications.

It will be appreciated that the same type of modification may be present in the same or varying degrees at several sites in a given polypeptide. Also, a given polypeptide may contain many types of modifications.

In general, as used herein, the term polypeptide encompasses all such modifications, particularly those that are present in polypeptides synthesized by expressing a polynucleotide in a host cell.

"Variant(s)" of polynucleotides or polypeptides, as the term is used herein, are polynucleotides or polypeptides that differ from a reference polynucleotide or polypeptide, respectively. Variants in this sense are described below and elsewhere in the present disclosure in greater detail.

(1) A polynucleotide that differs in nucleotide sequence from another, reference polynucleotide. Generally, differences are limited so that the nucleotide sequences of the reference and the variant are closely similar overall and, in many regions, identical.

As noted below, changes in the nucleotide sequence of the variant may be silent. That is, they may not alter the amino acids encoded by the polynucleotide. Where alterations are limited to silent changes of this type, a variant will encode a polypeptide with the same amino acid sequence as the reference. Also as noted below, changes in the nucleotide sequence of the variant may alter the amino acid sequence of a polypeptide encoded by the reference polynucleotide. Such nucleotide changes may result in amino acid substitutions, additions, deletions, fusions and truncations in the polypeptide encoded by the reference sequence, as discussed below.

(2) A polypeptide that differs in amino acid sequence from another, reference polypeptide. Generally, differences are limited so that the sequences of the reference and the variant are closely similar overall and, in many regions, identical.

A variant and reference polypeptide may differ in amino acid sequence by one or more substitutions, additions, deletions, fusions and truncations, which may be present in any combination.

"Fusion protein" as the term is used herein, is a protein encoded by two, often unrelated, fused genes or fragments thereof. European Patent Application No. EP-A-0 464 533 [Canadian counterpart Patent Application No. 2045869] discloses fusion proteins comprising various portions of constant region of immunoglobulin molecules together with another human protein or part thereof. In many cases, employing an immunoglobulin Fc region as a part of a fusion protein is advantageous for use in therapy and diagnosis resulting in, for example, improved pharmacokinetic properties [See, e.g., European Patent Application No. EP-A 0232 262]. For some uses, it would be desirable to be able to delete the Fc part after the fusion protein has been expressed, detected and purified. Accordingly, it may be desirable to link the two components of the fusion protein with a chemically or enzymatically cleavable linking region. This is the case when the Fc portion proves to be a hindrance to use in therapy and diagnosis, for example, when the fusion protein is to be used as an antigen for immunizations. In drug discovery, for example, human proteins, such as hIL-5, have been fused with Fc portions for use in high-throughput screening assays to identify antagonists of hIL-5. See, D. Bennett et al., *J. Mol. Recog.*, 8:52–58 (1995); and K. Johanson et al., *J. Biol. Chem.*, 270(16):9459–9471 (1995).

Thus, this invention also relates to genetically engineered soluble fusion proteins comprised of MADr3 or MADr4, or a portion thereof, and of various portions of the constant regions of heavy or light chains of immunoglobulins of various subclasses (IgG, IgM, IgA, IgE). Preferred as an immunoglobulin is the constant part of the heavy chain of human IgG, particularly IgG$_1$, where fusion takes place at the hinge region. In a particular embodiment, the Fc part can be removed simply by incorporation of a cleavage sequence which can be cleaved with blood clotting factor Xa. Furthermore, this invention relates to processes for the preparation of these fusion proteins by genetic engineering, and to the use thereof for diagnosis and therapy. A further aspect of the invention also relates to polynucleotides encoding such fusion proteins.

Membrane-bound receptors are particularly useful in the formation of fusion proteins. Such receptors are generally characterized as possessing three distinct structural regions: an extracellular domain, a transmembrane domain and a cytoplasmic domain. This invention contemplates the use of one or more of these regions as components of a fusion protein. Examples of such fusion protein technology can be found in International Patent Application Nos. WO94/29458 and WO94/22914.

"Binding molecules" (or otherwise called "interaction molecules" or "receptor component factors") refer to molecules, including ligands, that specifically bind to or-interact with polypeptides of the present invention. Such binding molecules are a part of the present invention. Binding molecules may also be non-naturally occurring, such as antibodies and antibody-derived reagents that bind specifically to polypeptides of the invention.

As known in the art, "similarity" between two polypeptides is determined by comparing the amino acid sequence and its conserved amino acid substitutes of one polypeptide to the sequence of a second polypeptide. Moreover, also known in the art is "identity" which means the degree of sequence relatedness between two polypeptide or two polynucleotide sequences as determined by the identity of the match between two lengths of such sequences. Both identity and similarity can be readily calculated [COMPUTATIONAL MOLECULAR BIOLOGY, Lesk, A.M., ed., Oxford University Press, New York, (1988); BIOCOMPUTING: INFORMATICS AND GENOME PROJECTS, Smith, D.W., ed., Academic Press, New York, (1993); COMPUTER ANALYSIS OF SEQUENCE DATA, PART I, Griffin, A. M., and Griffin, H.G., eds., Humana Press, New Jersey, (1994); SEQUENCE ANALYSIS IN MOLECULAR BIOLOGY, von Heinje, G., Academic Press, (1987); and SEQUENCE ANALYSIS PRIMER, Gribskov, M. and Devereux, J., eds., M Stockton Press, New York, (1991)]. While there exist a number of methods to measure identity and similarity between two polynucleotide or polypeptide sequences, the terms "identity" and "similarity" are well known to skilled artisans [H. Carillo and D. Lipton, *SIAM J. Applied Math.*, 48:1073 (1988)]. Methods commonly employed to determine identity or similarity between two sequences include, but are not limited to, those disclosed in Guide to Huge Computers, Martin J. Bishop, ed., Academic Press, San Diego, 1994, and H. Carillo and D. Lipton, *SIAM J. Applied Math.*, 48:1073 (1988). Preferred methods to determine identity are designed to give the largest match between the two sequences tested. Methods to determine identity and similarity are codified in computer programs. Preferred computer program methods to determine identity and similarity between two sequences include, but are not limited to, GCS program package [J. Devereux et al., *Nucl. Acids Res.*, 12(1):387 (1984)], BLAST, FASTA [S. F. Atschul et al., *J. Mol. Biol.*, 215:403 (1990)].

DETAILED DESCRIPTION OF THE INVENTION

The present invention relates to novel polypeptides putatively identified as human MAD polypeptides, and polynucleotides encoding same. In particular, the invention relates to polypeptides and polynucleotides of a novel human MADr3 and/or MADr4. This identification has been made as a result of amino acid sequence homology to other MAD proteins, such as Xenopus MAD1/2 or human MADr1. The clones of this invention code for novel MAD proteins, some of which might transduce the effects of TGF-β.

The invention relates especially to MADr3, a full length clone which covers the putative coding region of a MAD polypeptide, based on about 80% amino acid sequence homology to Xenopus MAD1/2 or human MADr1. MADr3 has nucleotide and amino acid sequences [SEQ ID NOS: 1 and 2, respectively] set out in FIGS. 1A–1D. The human cDNA of MADr3 and amino acid sequences encoded thereby are also provided in ATCC Deposit No. 98223 of plasmid pHSBHI91, which is herein referred to as "the deposited clone" or as the "cDNA of the deposited clone". It will be appreciated that the nucleotide and amino acid sequences set out in FIGS. 1A–1D are obtained by sequencing the cDNA of the deposited clone. Hence, the sequence of the deposited clone is controlling as to any discrepancies between the two, and any reference to the sequences of FIGS. 1A–1D includes a reference to the sequence of the human cDNA of the deposited clone.

Another partial clone for which two nucleotide sequences have been identified is designated MADr4 [SEQ ID NOS: 3 and 4]. The MADr4 fragments of FIGS. 2 and 3 show an 80% nucleotide homology with Xenopus MADr2, and a 90% nucleotide homology to Xenopus MADr2, respectively. FIG. 2 is believed to encode a partial amino acid sequence of MADr4.

Polynucleotides

The present invention provides an isolated nucleic acid (polynucleotide) which encodes the mature MADr3 polypeptide having the deduced amino acid sequence of FIGS. 1A–1D [SEQ ID NOS: 1 and 2] or the polypeptide encoded by the cDNA of the deposited clone.

Using the information provided herein, such as the polynucleotide sequence set out in FIGS. 1A–1D [SEQ ID NO: 1] or the polynucleotide sequences of FIGS. 2 and 3 [SEQ ID NOS: 3 and 4], a polynucleotide of the present invention encoding human MADr3 or MADr4 may be obtained using standard cloning and screening procedures, such as those for cloning cDNAs using mRNA from cells from human smooth muscle cells as starting material. Illustrative of the invention, the polynucleotide set out in FIGS. 1A–1D [SEQ ID NO: 1] was discovered in a commercially available cDNA library derived from human smooth muscle cells induced with Interleukin-1B, using the expressed sequence tag (EST) analysis [M. D. Adams et al., *Science*, 252:1651–1656 (1991); M. D. Adams et al., *Nature*, 355:632–634 (1992); M. D. Adams et al., *Nature*, 377 Supp:3–174 (1995)].

Human MADr3 or MADr4 of the invention are structurally related to other MAD proteins. For example, the cDNA sequence of MADr3 [FIGS. 1A–1D and SEQ ID NO: 1] contains an open reading frame encoding a polypeptide of 425 amino acids, which exhibits significant homology (~80%) to a number of members of the MAD gene family, including Xenopus MAD1/2 and human MADr1. This sequence encodes a protein having a deduced molecular weight of about 480 kDa.

Polynucleotides of the present invention may be in the form of RNA, such as MRNA, or in the form of DNA, including, for instance, CDNA and genomic DNA obtained by cloning or synthetic DNA produced by chemical synthetic techniques or by a combination thereof. The DNA may be double-stranded or single-stranded. Single-stranded DNA may be the coding strand, also known as the sense strand, or it may be the non-coding strand, also referred to as the anti-sense strand.

The sequence which encodes the mature MADr3 polypeptide may be identical to the coding sequence of the polynucleotide shown in FIGS. 1A–1D [SEQ ID NO: 1] or that of the deposited clone. It also may be a polynucleotide with a different coding sequence, which, as a result of the redundancy (degeneracy) of the genetic code, also encodes the same mature polypeptide of FIGS. 1A–1D [SEQ ID NO: 2] or the deposited cDNA.

A portion of the coding sequence which encodes the MADr4 polypeptide may be found within, or include either or both, the two partial sequences shown in FIGS. 2 and 3 (SEQ ID NOS:3 and 4). Alternatively, the coding sequence may include only one of the two partial sequences, i.e., FIG. 2, or the coding sequence may be a different coding sequence which coding sequence, as a result of the redundancy or degeneracy of the genetic code, encodes the same MADr4 polypeptide.

Polynucleotides of the present invention which encode the polypeptide of FIGS. 1A–1D or the polypeptide encoded by the deposited cDNA, may include, but are not limited to, the coding sequence for the mature polypeptide, by itself; the coding sequence for the mature polypeptide and additional coding sequences, such as those encoding a leader or secretory sequence, such as a pre-, or pro- or prepro- protein sequence; and the coding sequence of the mature polypeptide, with or without the aforementioned additional coding sequences, together with additional, non-coding sequences, including, but not limited to, introns and non-coding 5' and 3' sequences, such as the transcribed, non-translated sequences that play a role in transcription, and mRNA processing, including splicing and polyadenylation signals, for example, for ribosome binding and stability of mRNA. Coding sequences which provide additional functionalities may also be incorporated into the polypeptide.

The present invention also includes polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains.

Thus, for instance, the polypeptide may be fused in frame to a marker sequence, such as a peptide, which facilitates purification of the fused polypeptide. In certain preferred embodiments of this aspect of the invention, the marker sequence is a hexa-histidine peptide, such as the tag provided in the pQE-9 vector (Qiagen, Inc.) to provide for purification of the mature polypeptide fused to the marker in the case of a bacterial host. Or, for example, as described in Gentz et al., Proc. Natl. Acad. Sci., USA, 1989, 86:821–824, hexa-histidine provides for convenient purification of the fusion protein. In other embodiments, the marker sequence is a hemagglutinin (HA) tag, particularly when a mammalian host, e.g. COS-7 cells, is used. The HA tag corresponds to an epitope derived from influenza hemagglutinin protein, which has been described by Wilson et al., Cell, 1984, 37:767, for instance. Many other such tags are commercially available.

The polynucleotide which encodes for the partial polypeptide of MADr4 which may be encoded by the partial polynucleotide sequences of FIGS. 2 and 3 (SEQ ID NOS: 3 and 4) may include, but is not limited to the same types of sequences discussed immediately above.

In accordance with the foregoing, the term "polynucleotide encoding a polypeptide" as used herein encompasses polynucleotides which include, by virtue of the redundancy of the genetic code, any sequence encoding a polypeptide of the present invention, particularly the human MADr3 having the amino acid sequence set out in FIGS. 1A–1D [SEQ ID NO: 2]. The term includes only coding sequence for the polypeptide as well as a polynucleotide which includes additional coding and/or non-coding sequence.

The term also encompasses polynucleotides that include a single continuous region or discontinuous regions encoding the polypeptide (for example, interrupted by introns) together with additional regions, that also may contain coding and/or non-coding sequences.

The present invention further relates to variants of the herein above-described polynucleotides which encode for fragments, analogs and derivatives of the polypeptide having the deduced amino acid sequence of FIGS. 1A–1D (SEQ ID NOS: 2) or the polypeptides encoded by the cDNA of the deposited clone. A variant of the polynucleotide may be a naturally occurring variant of SEQ ID NOS: 1 and 2, or of the deposited clone, such as a naturally occurring allelic variant, or it may be a variant that is not known to occur naturally. As known in the art, an allelic variant is an alternate form of a polynucleotide sequence which may have a substitution, deletion or addition of one or more nucleotides, which does not substantially alter the function of the encoded polypeptide. Non-naturally occurring variants of the polynucleotide may be made by mutagenesis techniques, including those applied to polynucleotides, cells or organisms.

Among variants in this regard are variants that differ from the aforementioned polynucleotides by nucleotide substitutions, deletions or additions. The substitutions, deletions or additions may involve one or more nucleotides. The variants may be altered in coding or non-coding regions or both. Alterations in the coding regions may produce conservative or non-conservative amino acid substitutions, deletions or additions.

Among the particularly preferred embodiments of the invention in this regard are polynucleotides -encoding polypeptides having the amino acid sequence of MADr3 as set out in FIGS. 1A–1D [SEQ ID NO: 2]; the amino acid sequence encoded by the MADr4 sequences [SEQ ID NOS: 3 and 4], variants, analogs, derivatives and fragments thereof, and fragments of the variants, analogs and derivatives, or the same mature polypeptide encoded by the cDNA of the deposited clone.

Further particularly preferred in this regard are polynucleotides encoding MADr3 or MADr4 variants, analogs, derivatives and fragments, and variants, analogs and derivatives of the fragments, which have the amino acid sequence of the MADr3 polypeptide of FIGS. 1A–1D, or any polypeptide encoded by the polynucleotides of FIGS. 2 and 3 (SEQ ID NOS: 3 and 4) or the polypeptide encoded by the cDNA of the deposited clone. Such polypeptides in which several, a few, 5 to 10, 1 to 5, 1 to 3, 2, 1 or no amino acid residues are substituted, deleted or added, in any combination. Especially preferred among these are silent substitutions, additions, insertion and deletion variants, which do not alter the properties and activities of the MADr3 or MADr4. Also especially preferred in this regard are conservative substitutions. Most highly preferred are polynucleotides encoding polypeptides having the amino acid sequence of FIGS. 1A–1D, without substitutions.

Further preferred embodiments of the invention are polynucleotides that are at least about 80% identical to a polynucleotide encoding the MADr3 polypeptide having the amino acid sequence set out in FIGS. 1A–1D, and polynucleotides which are complementary to such polynucleotides. Most highly preferred are polynucleotides that comprise a region that is at least 85% identical to a polynucleotide encoding the MADr3 polypeptide of the human cDNA of the deposited clone and polynucleotides complementary thereto. In this regard, polynucleotides at least 90% identical to the same are particularly preferred, and those with at least 95% are especially preferred. Furthermore, those with at least 97% are highly preferred and those with at least 98–99% are most highly preferred, with at least 99% being the most preferred.

Particularly preferred embodiments in this respect, moreover, are polynucleotides which encode polypeptides which retain substantially the same biological function or activity as the mature polypeptide encoded by the cDNA of FIGS. 1A–1D, the deposited clone or the DNA of FIGS. 2 and 3.

The present invention further relates to polynucleotides that hybridize to the herein above-described sequences, particularly if there is at least 80% identity between the sequences as discussed above. In this regard, the present invention especially relates to polynucleotides which hybridize under stringent conditions to the herein above-described polynucleotides. As herein used, the term "stringent conditions" means hybridization will occur only if there is at least 95% and preferably at least 97% identity between the sequences.

As discussed additionally herein regarding polynucleotide assays of the invention, polynucleotides of the invention, including MADr3 and MADr4 fragments, may be used as hybridization probes for cDNA and genomic DNA, to isolate full-length cDNAs and genomic clones encoding MADr3 or MADr4, and to isolate cDNA and genomic clones of other genes that have a high sequence similarity to the human MADr3 or MADr4 gene and/or similar biological activity. Such probes generally will comprise at least 15 nucleotides. Preferably, such probes will have at least 30 nucleotides and may have at least 50 nucleotides. Particularly preferred probes will range between 30 and 50 nucleotides. The probe may also be used to identify a cDNA clone corresponding to a full length transcript and a genomic clone or clones that contain the complete MADr3 or MADr4 gene including regulatory and promotor regions, exons, and introns.

An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The polynucleotides which hybridize to the hereinabove described polynucleotides in a preferred embodiment encode polypeptides which either retain substantially the same biological function or activity as the mature polypeptide encoded by the cDNA of FIGS. 1A–1D (SEQ ID NO:1) or by the deposited cDNA, or by the partial cDNAs of FIGS. 2 and 3 (SEQ ID NOS: 3 and 4).

For example, such polynucleotides may be employed as probes for the polynucleotide of SEQ ID NO:1, of the polynucleotide of SEQ ID NOS: 2 and 3, for example, for recovery of the polynucleotide or as a diagnostic probe or as a PCR primer. For example, the coding region of the MADr3 or MADr4 gene may be isolated by screening using the known DNA sequence to synthesize an oligonucleotide probe. A labeled oligonucleotide having a sequence complementary to that of a gene of the present invention is then used to screen a library of human cDNA, genomic DNA or MRNA to determine the members of the library to which the probe hybridizes.

The polynucleotides and polypeptides of the present invention may be employed as research reagents and materials for discovery of treatments and diagnostics to human disease, as further discussed herein relating to polynucleotide assays.

The polynucleotides may encode a polypeptide which is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may facilitate protein trafficking, may prolong or shorten protein half-life or may facilitate manipulation of a protein for assay or production, among other things. As generally is the case in situ, the additional amino acids may be processed away from the mature protein by cellular enzymes. A precursor protein, having the mature form of the polypeptide fused to one or more prosequences, may be an inactive form of the polypeptide. When prosequences are removed, such inactive precursors generally are activated. Some or all of the prosequences may be removed before activation. Generally, such precursors are called proproteins.

In sum, a polynucleotide of the present invention may encode a mature protein, a mature protein plus a leader sequence (which may be referred to as a preprotein), a precursor of a mature protein having one or more prosequences which are not the leader sequences of a preprotein, or a preproprotein, which is a precursor to a proprotein, having a leader sequence and one or more prosequences, which generally are removed during processing steps that produce active and mature forms of the polypeptide.

Deposited materials

A deposit containing a human pHSBHI91 cDNA has been deposited with the American Type Culture Collection, 12301 Park Lawn Drive, Rockville, Md. 20852, USA, on Aug. 10, 1996 and assigned ATCC Deposit No. 98223. The human cDNA deposit is referred to herein as "the deposited clone" or as "the cDNA of the deposited clone."

The deposited material pHSBHI91 is a pBluescript SK (+/−) phagemid (Stragagene, Inc.) that contains the full length MADr3 cDNA inserted between the EcoRI and XhoI sites in the phagemid's multiple cloning site.

The deposit has been made under the terms of the Budapest Treaty on the International Recognition of the Deposit of Micro-organisms for purposes of Patent Procedure. The strain will be irrevocably and without restriction or condition released to the public upon the issuance of a patent. The deposit is provided merely as a convenience to those of skill in the art and is not an admission that a deposit is required for enablement, such as that required under 35 U.S.C. §112.

The sequence of the polynucleotides contained in the deposited material, as well as the amino acid sequence of the polypeptide encoded thereby, are incorporated herein by reference, and are controlling in the event of any conflict with any description of sequences herein.

A license may be required to make, use or sell the deposited materials, and no such license is hereby granted.

Polypeptides

The present invention relates to a human MADr3 polypeptide which has the deduced amino acid sequence of FIGS. 1A–1D [SEQ ID NO: 2] or which has the amino acid sequence encoded by the deposited cDNA. The invention also relates to variants, analogs, derivatives and fragments of these polypeptides, and variants, analogs and derivatives of the fragments. The terms "fragment," "derivative" and "analog" when referring to the polypeptide of FIGS. 1A–1D, means a polypeptide which retains essentially the same biological function or activity as such polypeptide, i.e., functions as a MADr3 or MADr4, or retains the ability to bind its ligand or binding molecules. Thus, an analog includes, for example, a proprotein which can be activated by cleavage of the proprotein portion to produce an active mature polypeptide. The polypeptide of the present invention may be a recombinant polypeptide, a natural polypeptide or a synthetic polypeptide. In certain preferred embodiments, it is a recombinant polypeptide.

The fragment, derivative or analog of the polypeptide of FIGS. 1A–1D or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code; (ii) one in which one or more of the amino acid residues includes a substituent group; (iii) one in which the mature polypeptide is fused with another compound, such as a compound to increase the half-life of the polypeptide (for example, polyethylene glycol); or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

Further, particularly preferred embodiments of the invention in this regard are polypeptides having the amino acid sequence of MADr4, variants, analogs, derivatives and fragments thereof, and variants, analogs and derivatives of the fragments which retain the activity/function of MADr4.

Among preferred variants are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe and Tyr.

Further particularly preferred in this regard are variants, analogs, derivatives and fragments, and variants, analogs and derivatives of the fragments, having the amino acid sequence of the MADr3 or MADr4 polypeptide of FIGS. 1A–1D, in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the MADr3 or MADr4. Also especially preferred in this regard are conservative substitutions. Most highly preferred are polypeptides having the amino acid sequence of FIGS. 1A–1D [SEQ ID NO: 2] without substitutions.

The polypeptides of the present invention include the polypeptide of SEQ ID NO: 2 (in particular the mature polypeptide) as well as polypeptides which have at least about 80% identity to the polypeptide of SEQ ID NO: 2and more preferably at least 90% similarity (more preferably at least 95% identity) to the polypeptide of SEQ ID NO: 2 and still more preferably at least 95% similarity (still more preferably at least 95% identity) to the polypeptide of SEQ ID NO: 2 and also include portions of such polypeptides with such portion of the polypeptide generally containing at least 30 amino acids and more preferably at least 50 amino acids.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention. Fragments may be "free-standing," i.e., not part of or fused to other amino acids or polypeptides, or they may be comprised within a larger polypeptide of which they form a part or region. When comprised within a larger polypeptide, the presently discussed fragments most preferably form a single continuous region. However, several fragments may be comprised within a single larger polypeptide. For instance, certain preferred embodiments relate to a fragment of a MADr3 or MADr4 polypeptide of the present invention comprised within a precursor polypeptide designed for expression in a host and having heterologous pre- and pro-polypeptide regions fused to the amino terminus of the MADr3 or MADr4 fragment and an additional region fused to the carboxyl terminus of the fragment. Therefore, fragments in one aspect of the meaning intended herein, refers to the portion or portions of a fusion polypeptide or fusion protein derived from MADr3 or MADr4.

As representative examples of polypeptide fragments of the invention, there may be mentioned those which have from about 5–15, 10–20, 15–40, 30–55, 41–75, 41–80, 41–90, 50–100, 75–100, 90–115, 100–125, and 110–113 amino acids in length. In this context "about" includes the particularly recited range and ranges larger or smaller by several, a few, 5, 4, 3, 2 or 1 amino acid residues at either extreme or at both extremes. For instance, about 40–90 amino acids in this context means a polypeptide fragment of 40 plus or minus several, a few, 5, 4, 3, 2 or 1 amino acid residues to 90 plus or minus several a few, 5, 4, 3, 2 or 1 amino acid residues, i.e., ranges as broad as 40 minus several amino acids to 90 plus several amino acids to as narrow as 40 plus several amino acids to 90 minus several amino acids. Highly preferred in this regard are the recited ranges plus or minus as many as 5 amino acids at either or at both extremes. Particularly highly preferred are the recited ranges plus or minus as many as 3 amino acids at either or at both the recited extremes. Especially particularly highly preferred are ranges plus or minus 1 amino acid at either or at both extremes or the recited ranges with no additions or deletions. Most highly preferred of all in this regard are fragments from about 5–15, 10–20, 15–40, 30–55, 41–75, 41–80, 41–90, 50–100, 75–100, 90–115, 100–125, and 110–113 amino acids long.

Among especially preferred fragments of the invention are truncation mutants of MADr3 or MADr4. Truncation mutants include MADr3 polypeptides having the amino acid sequence of FIGS. 1A–1D, or of variants or derivatives thereof, except for deletion of a continuous series of residues (that is, a continuous region, part or portion) that includes the amino terminus, or a continuous series of residues that includes the carboxyl terminus or, as in double truncation mutants, deletion of two continuous series of residues, one including the amino terminus and one including the carboxyl terminus. Fragments having the size ranges set out above also are preferred embodiments of truncation fragments, which are especially preferred among fragments generally.

Also preferred in this aspect of the invention are fragments characterized by structural or functional attributes of MADr3 or MADr4. Preferred embodiments of the invention in this regard include fragments that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of MADr3 or MADr4.

Among highly preferred fragments in this regard are those that comprise regions of MADr3 or MADr4 that combine several structural features, such as several of the features set out above. In this regard, the regions defined by the residues about 10 to about 20, about 40 to about 50, about 70 to about 90 and about 100 to about 113 of FIGS. 1A–1D, which all are characterized by amino acid compositions highly characteristic of turn-regions, hydrophilic regions, flexible-regions, surface-forming regions, and high antigenic index-regions, are especially highly preferred regions. Such regions may be comprised within a larger polypeptide or may be by themselves a preferred fragment of the present invention, as discussed above. It will be appreciated that the term "about" as used in this paragraph has the meaning set out above regarding fragments in general.

Further preferred regions are those that mediate activities of MADr3 or MADr4. Most highly preferred in this regard are fragments that have a chemical, biological or other activity of MADr3 or MADr4, including those with a similar activity or an improved activity, or with a decreased undesirable activity. Highly preferred in this regard are fragments that contain regions that are homologs in sequence, or in position, or in both sequence and to active regions of related polypeptides, such as the human MADr1 polypeptide. Among particularly preferred fragments in these regards are truncation mutants, as discussed above, or fragments comprising various domains of the polypeptide.

It will be appreciated that the invention also relates to, among others, polynucleotides encoding the aforementioned fragments, polynucleotides that hybridize to polynucleotides encoding the fragments, particularly those that hybridize under stringent conditions, and polynucleotides, such as PCR primers, for amplifying polynucleotides that encode the fragments. In these regards, preferred polynucleotides are those that correspond to the preferred fragments, as discussed above.

Vectors, Host Cells, Expression

The present invention also relates to vectors which include polynucleotides of the present invention, host cells which are genetically engineered with vectors of the invention and the production of polypeptides of the invention by recombinant techniques.

Host cells can be genetically engineered to incorporate polynucleotides and express polypeptides of the present invention. For instance, polynucleotides may be introduced into host cells using well known techniques of infection, transduction, transfection, transvection and transformation. Unless otherwise stated, transformation was performed as described in the method of Graham, F. and Van der Bb, A., Virology, 52:456–457 (1973).

The polynucleotides may be introduced alone or with other polynucleotides. Such other polynucleotides may be introduced independently, co-introduced or introduced joined to the polynucleotides of the invention. Thus, for instance, polynucleotides of the invention may be transfected into host cells with another, separate polynucleotide encoding a selectable marker, using standard techniques for co-transfection and selection in, for instance, mammalian cells. In this case the polynucleotides generally will be stably incorporated into the host cell genome.

Alternatively, the polynucleotides may be joined to a vector containing a selectable marker for propagation in a host. The vector construct may be introduced into host cells by the aforementioned techniques. Generally, a plasmid vector is introduced as DNA in a precipitate, such as a calcium phosphate precipitate, or in a complex with a charged lipid. Electroporation may also be used to introduce polynucleotides into a host. If the vector is a virus, it may be packaged in vitro or introduced into a packaging cell and the packaged virus may be transduced into cells. A wide variety of techniques suitable for making polynucleotides and for introducing polynucleotides into cells in accordance with this aspect of the invention are well known and routine to those of skill in the art. Such techniques are reviewed at length in Sambrook et al, which is illustrative of the many laboratory manuals that detail these techniques.

In accordance with this aspect of the invention the vector may be, for example, a plasmid vector, a single or double-stranded phage vector, or a single or double-stranded RNA or DNA viral vector. Such vectors may be introduced into cells as polynucleotides, preferably DNA, by well known techniques for introducing DNA and RNA into cells. The vectors, in the case of phage and viral vectors may also be and preferably are introduced into cells as packaged or encapsidated virus by well known techniques for infection and transduction. Viral vectors may be replication competent or replication defective. In the latter case, viral propagation generally will occur only in complementing host cells.

Preferred among vectors, in certain respects, are those for expression of polynucleotides and polypeptides of the present invention. Generally, such vectors comprise cis-acting control regions effective for expression in a host operatively linked to the polynucleotide to be expressed. Appropriate trans-acting factors are either supplied by the host, supplied by a complementing vector or supplied by the vector itself upon introduction into the host.

In certain preferred embodiments in this regard, the vectors provide for specific expression. Such specific expression may be inducible expression or expression only in certain types of cells or both inducible and cell-specific expression. Particularly preferred among inducible vectors are vectors that can be induced for expression by environmental factors that are easy to manipulate, such as temperature and nutrient additives. A variety of vectors suitable to this aspect of the invention, including constitutive and inducible expression vectors for use in prokaryotic and eukaryotic hosts, are well known and employed routinely by those of skill in the art.

The engineered host cells can be cultured in conventional nutrient media, which may be modified as appropriate for, inter alia, activating promoters, selecting transformants or amplifying genes. Culture conditions, such as temperature, pH and the like, previously used with the host cell selected for expression, generally will be suitable for expression of polypeptides of the present invention as will be apparent to those of skill in the art. A great variety of expression vectors can be used to express a polypeptide of the invention. Such vectors include chromosomal, episomal and virus-derived vectors e.g., vectors derived from bacterial plasmids, bacteriophages, yeast episomes, yeast chromosomal elements, and viruses such as baculoviruses, papova viruses, SV40, vaccinia viruses, adenoviruses, fowl pox viruses, pseudorabies viruses and retroviruses, and vectors derived from combinations thereof, such as those derived from plasmid and bacteriophage genetic elements, cosmids and phagemids. Generally, any vector suitable to maintain, propagate or express polynucleotides to produce a polypeptide in a host may be used for expression in this regard.

The appropriate DNA sequence may be inserted into the vector by any of a variety of well-known and routine techniques. In general, a DNA sequence for expression is joined to an expression vector by cleaving the DNA sequence and the expression vector with one or more restriction endonucleases and then joining the restriction fragments together using T4 DNA ligase. Procedures for restriction and ligation that can be used to this end are well known and routine to those of skill. Suitable procedures in this regard, and for constructing expression vectors using alternative techniques, which also are well known and routine to those skilled in the art, are set forth in great detail in Sambrook et al.

The DNA sequence in the expression vector is operatively linked to appropriate expression control sequence(s), including, for instance, a promoter to direct MRNA transcription. Representatives of such promoters include the phage lambda PL promoter, the E. coli lac, trp and tac promoters, the SV40 early and late promoters and promoters of retroviral LTRs, to name just a few of the well-known promoters. It will be understood that numerous other promoters useful in this aspect of the invention are well known and may be routinely employed by those of skill in the manner illustrated by the discussion and the examples herein.

In general, expression constructs will contain sites for transcription initiation and termination, and, in the transcribed region, a ribosome binding site for translation. The coding portion of the mature transcripts expressed by the constructs will include a translation initiating AUG at the beginning and a termination codon appropriately positioned at the end of the polypeptide to be translated.

In addition, the constructs may contain control regions that regulate as well as engender expression. Generally, in accordance with many commonly practiced procedures, such regions will operate by controlling transcription. Examples include repressor binding sites and enhancers, among others. Vectors for propagation and expression generally will include selectable markers. Selectable marker genes provide a phenotypic trait for selection of transformed host cells. Preferred markers include, but are not limited to, dihydrofolate reductase or neomycin resistance for eukaryotic cell culture, and tetracycline or ampicillin resistance genes for culturing *E. coli* and other bacteria. Such markers may also be suitable for amplification. Alternatively, the vectors may contain additional markers for this purpose.

The vector containing the appropriate DNA sequence as described elsewhere herein, as well as an appropriate promoter, and other appropriate control sequences, may be introduced into an appropriate host using a variety of well known techniques suitable for expression therein of a desired polypeptide. Representative examples of appropriate hosts include bacterial cells, such as *E. coli, Streptomyces* and *Salmonella typhimurium* cells; fungal cells, such as yeast cells; insect cells such as Drosophila S2 and Spodoptera Sf9 cells; animal cells such as CHO, COS and Bowes melanoma cells; and plant cells. Hosts of a great variety of expression constructs are well known, and those of skill will be enabled by the present disclosure to routinely select a host for expressing a polypeptide in accordance with this aspect of the present invention.

More particularly, the present invention also includes recombinant constructs, such as expression constructs, comprising one or more of the sequences described above. The constructs comprise a vector, such as a plasmid or viral vector, into which such a sequence of the invention has been inserted. The sequence may be inserted in a forward or reverse orientation. In certain preferred embodiments in this regard, the construct further comprises regulatory sequences, including, for example, a promoter, operably linked to the sequence. Large numbers of suitable vectors and promoters are known to those of skill in the art, and there are many commercially available vectors suitable for use in the present invention.

The following vectors, which are commercially available, are provided by way of example. Among vectors preferred for use in bacteria are pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. These vectors are listed solely by way of illustration of the many commercially available and well known vectors that are available to those of skill in the art for use in accordance with this aspect of the present invention. It will be appreciated that any other plasmid or vector suitable for, for example, introduction, maintenance, propagation or expression of a polynucleotide or polypeptide of the invention in a host may be used in this aspect of the invention.

Promoter regions can be selected from any desired gene using vectors that contain a reporter transcription unit lacking a promoter region, such as a chloramphenicol acetyl transferase ("CAT") transcription unit, downstream of a restriction site or sites for introducing a candidate promoter fragment; i.e., a fragment that may contain a promoter. As is well known, introduction into the vector of a promoter-containing fragment at the restriction site upstream of the CAT gene engenders production of CAT activity, which can be detected by standard CAT assays. Vectors suitable to this end are well known and readily available. Two examples of such vectors include pKK232-8 and pCM7. Thus, promoters for expression of polynucleotides of the present invention include not only well known and readily available promoters, but also promoters that may be readily obtained by the foregoing technique, using a reporter gene.

Among known bacterial promoters suitable for expression of polynucleotides and polypeptides in accordance with the present invention are the *E. coli* lacI and lacZ promoters, the T3 and T7 promoters, the gpt promoter, the lambda PR, PL promoters and the trp promoter. Among known eukaryotic promoters suitable in this regard are the CMV immediate early promoter, the HSV thymidine kinase promoter, the early and late SV40 promoters, the promoters of retroviral LTRs, such as those of the Rous Sarcoma Virus ("RSV"), and metallothionein promoters, such as the mouse metallothionein-I promoter. Selection of appropriate vectors and promoters for expression in a host cell is a well known procedure and the requisite techniques for construction of expression vectors, introduction of the vector into the host and expression in the host are routine skills in the art.

The present invention also relates to host cells containing the above-described constructs. The host cell can be a higher eukaryotic cell, such as a mammalian cell, a lower eukaryotic cell, such as a yeast cell, or a prokaryotic cell, such as a bacterial cell. Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al. BASIC METHODS IN MOLECULAR BIOLOGY, (1986).

Constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al.

Generally, recombinant expression vectors will include origins of replication, a promoter derived from a highly-expressed gene to direct transcription of a downstream structural sequence, and a selectable marker to permit isolation of vector containing cells following exposure to the vector. Among suitable promoters are those derived from the genes that encode glycolytic enzymes such as 3-phosphoglycerate kinase ("PGK"), α-factor, acid phosphatase, and heat shock proteins, among others. Selectable markers include the ampicillin resistance gene of *E. coli* and the trpl gene of *S. cerevisiae*.

Transcription of DNA encoding the polypeptides of the present invention by higher eukaryotes may be increased by inserting an enhancer sequence into the vector. Enhancers are cis-acting elements of DNA, usually from about 10 to 300 bp, that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

A polynucleotide of the invention encoding the heterologous structural sequence of a polypeptide of the invention generally will be inserted into the vector using standard techniques so that it is operably linked to the promoter for expression. The polynucleotide will be positioned so that the transcription start site is located appropriately 5' to a ribosome binding site. The ribosome binding site will be 5' to the AUG that initiates translation of the polypeptide to be expressed. Generally, there will be no other open reading frames that begin with an initiation codon, usually AUG, and lie between the ribosome binding site and the initiation codon. Also, generally, there will be a translation stop codon at the end of the polypeptide and a polyadenylation signal and transcription termination signal appropriately disposed at the 3' end of the transcribed region.

Appropriate secretion signals may be incorporated into the expressed polypeptide for secretion of the translated protein into the lumen of the endoplasmic reticulum, the periplasmic space or the extracellular environment. The signals may be endogenous to the polypeptide or heterologous.

The polypeptide may be expressed in a modified form, such as a fusion protein, and may include not only secretion signals but also additional heterologous functional regions. Thus, for example, a region of additional amino acids, particularly charged amino acids, may be added to the N-terminus of the polypeptide to improve stability and persistence in the host cell during purification or subsequent handling and storage. A region may also be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art.

Suitable prokaryotic hosts for propagation, maintenance or expression of polynucleotides and polypeptides in accordance with the invention include *Escherichia coli, Bacillus subtilis* and *Salmonella typhimurium*. Various species of Pseudomonas, Streptomyces, and Staphylococcus are also suitable hosts in this regard. Moreover, many other hosts also known to those of skill may be employed in this regard.

As a representative but non-limiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). In these vectors, the pBR322 "backbone" sections are combined with an appropriate promoter and the structural sequence to be expressed.

Following transformation of a suitable host strain, the host strain is grown to an appropriate cell density. Where the selected promoter is inducible, it is induced by appropriate means (e.g., temperature shift or exposure to chemical inducer) and cells are cultured for an additional period. Cells typically then are harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents. Such methods are well known to those skilled in the art.

Various mammalian cell culture systems can be employed for expression, as well. Examples of mammalian expression systems include, without limitation, the C127, 3T3, CHO, HeLa, human kidney 293 and BHK cell lines. and the COS-7 line of monkey kidney fibroblasts, described by Gluzman et al., Cell, 1981, 23:175. Mammalian expression vectors will comprise an origin of replication, a suitable promoter and enhancer, and any necessary ribosome binding sites, polyadenylation sites, splice donor and acceptor sites, transcriptional termination sequences, and 51 flanking non-transcribed sequences that are necessary for expression. In certain preferred embodiments, DNA sequences derived from the SV40 splice sites and the SV40 polyadenylation sites are used for required non-transcribed genetic elements.

The MADr3 or MADr4 polypeptide can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Well known techniques for refolding proteins may be employed to regenerate active conformation when the polypeptide is denatured during isolation and or purification.

Polypeptides of the present invention include naturally purified polypeptides, polypeptides produced by chemical synthetic procedures, and polypeptides produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or non-glycosylated. In addition, polypeptides of the invention may include an initial modified methionine residue, in some cases as a result of host-mediated processes.

MADr3 or MADr4 polynucleotides and polypeptides may be used in accordance with the present invention for a variety of applications, particularly those that make use of the chemical and biological properties of MADr3 or MADr4. Additional applications relate to diagnosis and to treatment of disorders of cells, tissues and organisms. These aspects of the invention are illustrated further by the following discussion.

Polynucleotide Assays

This invention is also related to the use of MADr3 or MADr4 polynucleotides to detect complementary polynucleotides for use, for example, as a diagnostic reagent. Detection of a mutated form of a gene encoding MADr3 or MADr4 associated with a dysfunction will provide a diagnostic tool that can add to or define diagnosis of a disease or susceptibility to a disease which results from under-expression, over-expression or altered expression of MADr3 or MADr4. Such diseases may include, for example, improper wound healing, improper neurological functioning, ocular disorders, kidney and liver disorders, and cancers.

Individuals carrying mutations in the human MADr3 or MADr4 gene may be detected at the DNA level by a variety of techniques. Nucleic acids for diagnosis may be obtained from a patient's cells, such as from blood, urine, saliva, tissue biopsy or autopsy material. The genomic DNA may be used directly for detection or may be amplified enzymatically by using polymerase chain reaction (PCR) [Saiki et al., Nature, 324:163–166 (1986)] prior to analysis. RNA or cDNA may also be used in similar fashion. As an example, PCR primers complementary to the nucleic acid encoding MADr3 or MADr4 can be used to identify and analyze MADr3 or MADr4 expression and mutations. For example, deletions and insertions can be detected by a change in size of the amplified product in comparison to the normal genotype. Point mutations can be identified by hybridizing amplified DNA to radiolabeled MADr3 or MADr4 RNA or, radiolabeled MADr3 or MADr4 antisense DNA sequences. Perfectly matched sequences can be distinguished from mismatched duplexes by RNase A digestion or by differences in melting temperatures.

Sequence differences between a reference gene and genes having mutations may also be revealed by direct DNA sequencing. In addition, cloned DNA segments. may be employed as probes to detect specific DNA segments. The sensitivity of such methods can be greatly enhanced by appropriate use of PCR or other amplification methods. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alterations in electrophoretic mobility of DNA fragments in gels, with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures [see, e.g., Myers et al., Science, 230:1242 (1985)].

Sequence changes at specific locations may also be revealed by nuclease protection assays, such as RNase and S1 protection or the chemical cleavage method [e.g., Cotton et al., Proc. Natl. Acad. Sci., USA, 85:4397–4401 (1985)].

Thus, the detection of a specific DNA sequence may be achieved by methods such as hybridization, RNase protection, chemical cleavage, direct DNA sequencing or the use of restriction enzymes, (e.g., restriction fragment length polymorphisms ("RFLP") and Southern blotting of genomic DNA.

The invention provides a process for diagnosing or determining a susceptibility to MAD protein-related dysfunctions or diseases including, but not limited to, those specifically identified hereinbefore. A mutation in the MADr3 or MADr4 gene indicates a susceptibility to such dysfunctions or diseases including, but not limited to, cancers of the colon, breast, liver, prostate, kidney and bone, and the nucleic acid sequences described above may be employed in an assay for ascertaining such susceptibility. Thus, for example, the assay may be employed to determine a mutation in a human MADr3 or MADr4 gene as herein described, such as a substitution, deletion, truncation, insertion, frame shift, etc., with such mutation being indicative of a susceptibility to any of the dysfunctions or diseases recited above.

The invention provides a process for diagnosing such aforementioned MAD polypeptide-related diseases comprising determining from a sample derived from a patient an abnormally decreased or increased level of expression of polynucleotide having the sequence of FIGS. 1A–1D [SEQ ID NO: 1], of the deposited cDNA, or of FIGS. 2 and 3 [SEQ ID NOS: 3 and 4]. Decreased or increased expression of polynucleotide can be measured using any of the methods well known in the art for the quantitation of polynucleotides, such as, for example, PCR, RT-PCR, RNase protection, Northern blotting and other hybridization methods.

In addition to more conventional gel-electrophoresis and DNA sequencing, mutations can also be detected by in situ analysis.

Chromosome Assays

The sequences of the present invention are also valuable for chromosome identification. The sequence is specifically targeted, to and can hybridize with, a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–30 bp) from the cDNA. Computer analysis of the 3' untranslated region is used to rapidly select primers that do not span more than one exon in the genomic DNA, because primers that span more than one exon could complicate the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can be used similarly to map to the chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNAs as short as 50 to 60 bases. For a review of this technique, see Verma et al., HUMAN CHROMOSOMES: A MANUAL-OF BASIC TECHNIQUES, PERGAMON PRESS, NEW YORK, 1988.

As an example of how this technique is performed, MADr3 or MADr4 DNA is digested and purified with QIAEX II DNA purification kit (QIAGEN, Inc., Chatsworth, Calif.) and ligated to Super Cosl cosmid vector (STRATAGENE, La Jolla, Calif.). DNA is purified using Qiagen Plasmid Purification Kit (QIAGEN Inc., Chatsworth, Calif.) and 1 mg is labeled by nick translation in the presence of Biotin-dATP using BioNick Labeling Kit (GibcoBRL, Life Technologies Inc., Gaithersburg, Md.). Biotinylation is detected with GENE-TECT Detection System (CLONTECH Laboratories, Inc. Palo Alto, Calif.). In situ hybridization is performed on slides using ONCOR Light Hybridization Kit (ONCOR, Gaithersberg, Md.) to detect single copy sequences on metaphase chromosomes. Peripheral blood of normal donors is cultured for three days in RPMI 1640 supplemented with 20% FCS, 3% PHA and penicillin/streptomycin, synchronized with 10–7 M methotrexate for 17 hours, and washed twice with unsupplemented RPMI. Cells are then incubated with 10–3 M thymidine for 7 hours. The cells are arrested in metaphase after a 20 minute incubation with colcemid (0.5 mg/ml) followed by hypotonic lysis in 75 mM KCl for 15 minutes at 37° C. Cell pellets are then spun out and fixed in Carnoy's fixative (3:1 methanol/acetic acid).

Metaphase spreads are prepared by adding a drop of the suspension onto slides and air drying the suspension. Hybridization is performed by adding 100 ng of probe suspended in 10 ml of hybridization mix (50% formamide, 2×SSC, 1% dextran sulfate) with blocking human placental DNA (1 mg/ml). Probe mixture is denatured for 10 minutes in a 70° C. water bath and incubated for 1 hour at 37° C., before placement on a prewarmed (37° C.) slide, previously denatured in 70% formamide/2×SSC at 70° C., dehydrated in ethanol series, and chilled to 4° C.

Slides are incubated for 16 hours at 37° C. in a humidified chamber. Slides are washed in 50% formamide/2×SSC for 10 minutes at 41° C. and 2×SSC for 7 minutes at 37° C. Hybridization probe is detected by incubation of the slides with FITC-Avidin (ONCOR, Gaithersberg, Md.), according to the manufacturer's protocol. Chromosomes are counterstained with propridium iodine suspended in mounting medium. Slides are visualized using a Leitz ORTHOPLAN 2-epifluorescence microscope and five computer images are taken using a Imagenetics Computer and MacIntosh printer.

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

It is then necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with-the disease could be one of between 50 and 500 potential causative genes, assuming 1 megabase mapping resolution and one gene per 20 kb.

Polypeptide Assays

The present invention also relates to diagnostic assays for detecting altered levels of MADr3 or MADr4 protein in cells and tissues. Such assays may be quantitative or qualitative, Thus, for instance, a diagnostic assay in accordance with the invention for detecting over-expression of MADr3 or MADr4 protein compared to normal control tissue samples may be used to detect the presence of certain disease conditions such as cancers, and other diseases.

Assay techniques that can be used to determine levels of a protein, such as an MADr3 or MADr4 protein of the present invention, in a sample derived from a host are well-known to those of skill in the art. Such assay methods include radioimmunoassays, competitive-binding assays, Western Blot analysis and ELISA assays. Among these, ELISAs are frequently preferred. An ELISA assay initially comprises preparing an antibody specific to MADr3 or MADr4, preferably a monoclonal antibody. In addition a reporter antibody generally is prepared which binds to the monoclonal antibody. The reporter antibody is attached to a detectable reagent such as a radioactive, fluorescent or enzymatic reagent, e.g., horseradish peroxidase enzyme.

To carry out an ELISA, a sample is removed from a host and incubated on a solid support, e.g. a polystyrene dish, that binds the proteins in the sample. Any free protein binding sites on the dish are then covered by incubating with a non-specific protein such as bovine serum albumin. The monoclonal antibody is then incubated in the dish during which time the monoclonal antibodies attach to any MADr3 or MADr4 proteins attached to the polystyrene dish. Unbound monoclonal antibody is washed out with buffer. The reporter antibody linked to horseradish peroxidase is placed in the dish resulting in binding of the reporter antibody to any monoclonal antibody bound to MADr3 or MADr4. Unattached reporter antibody is then washed out. Reagents for peroxidase activity, including a calorimetric substrate, are then added to the dish. Immobilized peroxidase, linked to MADr3 or MADr4 through the primary and secondary antibodies, produces a colored reaction product. The amount of color developed in a given time period indicates the amount of MADr3 or MADr4 protein present in the sample. Quantitative results typically are obtained by reference to a standard curve.

A competition assay may also be employed to determine levels of the polypeptide of the present invention in a sample derived from the hosts. Such an assay comprises isolating cytoplasmic proteins which contain or over-express the polypeptide of the present invention. A test sample containing the polypeptides of the present invention which have been labeled, are then added to the purified cytoplasmic proteins and then incubated for a set period of time. Also added to the reaction mixture is a sample derived from a host which is suspected of containing the polypeptide of the present invention. The reaction mixtures are then passed through a filter which is rapidly washed and the bound radioactivity is then measured to determine the amount of competition for the polypeptides and therefore the amount of the polypeptides of the present invention in the sample.

Another competition assay may involve antibodies specific to MADr3 or MADr4, which are attached to a solid support and labeled MADr3 or MADr4 and a sample derived from the host are passed over the solid support. The amount of detected label attached to the solid support can be correlated to a quantity of MADr3 or MADr4 in the sample.

Antibodies

The polypeptides, their fragments or other derivatives, or analogs thereof, or cells expressing them can also be used as immunogens to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptide itself. In this manner, even a sequence encoding only a fragment of the polypeptide can be used to generate antibodies binding the whole native polypeptide. Such antibodies can then be used to isolate the polypeptide from tissue expressing that polypeptide.

For preparation of monoclonal antibodies, any technique which provides antibodies produced by continuous cell line cultures can be used. Examples include the hybridoma technique [G. Kohler and C. Milstein, *Nature*, 256:495–497 (1975)], the trioma technique, the human B-cell hybridoma technique [Kozbor et al., *Immunology Today*, 4:72 (1983)], and the EBV-hybridoma technique [Cole et al., MONOCLONAL ANTIBODIES AND CANCER THERAPY, pg. 77–96, Alan R. Liss, Inc., (1985)].

Techniques described for the production of single chain antibodies [U.S. Pat. No. 4,946,778] can also be adapted to produce single chain antibodies to immunogenic polypeptide products of this invention. Also, transgenic mice, or other organisms including other mammals, may be used to express humanized antibodies to immunogenic polypeptide products of this invention.

The above-described antibodies may be employed to isolate or to identify clones expressing the polypeptide or purify the polypeptide of the present invention by attachment of the antibody to a solid support for isolation and/or purification by affinity chromatography.

Antibodies against MADr3 or MADr4 may also be employed to inhibit dysfunctions or diseases such as the diseases mentioned hereinabove, among others.

Antibodies specific to MADr3 or MADr4 may be used for cancer diagnosis and therapy, since many types of cancer cells upregulate various members of the TGF-β family during the process of neoplasia or hyperplasia. These antibodies bind to and inactivate MAD proteins, which signal the activation of TGF-β. Monoclonal antibodies against the MAD polypeptides of this invention can be used for both the diagnosis and therapy of certain disorders including (but not limited to) hyperplastic and neoplastic growth abnormalities. Upregulation of growth factor expression by neoplastic tissues forms the basis for a variety of serum assays which detect increases in growth factor in the blood of affected patients. These assays are typically applied not only in diagnostic settings, but are applied in prognostic settings as well (to detect the presence of occult tumor cells following surgery, chemotherapy, etc).

MADr3 or MADr4 Binding Molecules and Assays

MADr3 or MADr4 can be used to isolate proteins which interact with it; and this interaction can be a target for interference. Inhibitors of protein-protein interactions between MADr3 or MADr4 and other factors could lead to the development of pharmaceutical agents for the modulation of MADr3 or MADr4 activity.

Thus, this invention also provides a method for identification of binding molecules to MADr3 or MADr4. Genes encoding proteins for binding molecules to MADr3 or MADr4 can be identified by numerous methods known to those of skill in the art, for example, ligand panning and FACS sorting. Such methods are described in many laboratory manuals such as, for instance, Coligan et al., CURRENT PROTOCOLS IN IMMUNOLOGY 1, Chapter 5 (1991).

For example, the yeast two-hybrid system provides methods for detecting the interaction between a first test protein and a second test protein, in vivo, using reconstitution of the activity of a transcriptional activator. The method is disclosed in U.S. Pat. No. 5,283,173; reagents are available from Clontech and Stratagene. Briefly, MADr3 or MADr4 cDNA is fused to a Gal4 transcription factor DNA binding domain and expressed in yeast cells. cDNA library members obtained from cells of interest are fused to a transactivation domain of Gal4. cDNA clones which express proteins which can interact with MADr3 or MADr4 will lead to reconstitution of Gal4 activity and transactivation of expression of a reporter gene such as Gal1-lacZ.

An alternative method involves screening of lambda gt11 or lambda ZAP (Stratagene) or equivalent cDNA expression libraries with recombinant MADr3 or MADr4. Recombinant MADr3 or MADr4 protein or fragments thereof are fused to small peptide tags such as FLAG, HSV or GST. The peptide tags can possess convenient phosphorylation sites for a kinase such as heart muscle creatine kinase or they can be biotinylated. Recombinant MADr3 or MADr4 can be phosphorylated with $^{32}$[P] or used unlabeled and detected with streptavidin or antibodies against the tags. Lambda gt11 cDNA expression libraries are made from cells of interest and are incubated with the recombinant MADr3 or MADr4, washed and cDNA clones which interact with MADr3 or MADr4 isolated. Such methods are routinely used by skilled artisans. See, e.g., Sambrook et al.

Another method is the screening of a mammalian expression library. In this method, cDNAs are cloned into a vector between a mammalian promoter and polyadenylation site and transiently transfected in COS or 293 cells. Forty-eight hours later, the binding protein is detected by incubation of fixed and washed cells with labeled MADr3 or MADr4. In a preferred embodiment, the MADr3 or MADr4 is iodinated, and any bound MADr3 or MADr4 is detected by autoradiography. See Sims et al., *Science*, 1988, 241:585–589 and McMahan et al., *EMBO J.*, 1991, 10:2821–2832. In this manner, pools of cDNAs containing the cDNA encoding the binding protein of interest can be selected and the cDNA of interest can be isolated by further subdivision of each pool followed by cycles of transient transfection, binding and autoradiography. Alternatively, the cDNA of interest can be isolated by transfecting the entire cDNA library into mammalian cells and panning the cells on a dish containing MADr3 or MADr4 bound to the plate. Cells which attach after washing are lysed and the plasmid DNA isolated, amplified in bacteria, and the cycle of transfection and panning repeated until a single cDNA clone is obtained. See Seed et al, *Proc. Natl. Acad. Sci. USA*, 1987, 84:3365 and Aruffo et al., *EMBO J.*, 1987, 6:3313. If the binding protein is secreted, its cDNA can be obtained by a similar pooling strategy once a binding or neutralizing assay has been established for assaying supernatants from transiently transfected cells. General methods for screening supernatants are disclosed in Wong et al., *Science*, 1985, 228:810–815.

Another method involves isolation of proteins interacting with MADr3 or MADr4 directly from cells. Fusion proteins of MADr3 or MADr4 with GST or small peptide tags are made and immobilized on beads. Biosynthetically labeled or unlabeled protein extracts from the cells of interest are prepared, incubated with the beads and washed with buffer. Proteins interacting with MADr3 or MADr4 are eluted specifically from the beads and analyzed by SDS-PAGE. Binding partner primary amino acid sequence data are obtained by microsequencing. Optionally, the cells can be treated with agents that induce a functional response such as tyrosine phosphorylation of cellular proteins. An example of such an agent would be a growth factor or cytokine such as interleukin-2.

Another method is immunoaffinity purification. Recombinant MADr3 or MADr4 is incubated with labeled or unlabeled cell extracts and immunoprecipitated with anti-MADr3 or MADr4 antibodies. The immunoprecipitate is recovered with protein A-Sepharose and analyzed by SDS-PAGE. Unlabelled proteins are labeled by biotinylation and detected on SDS gels with streptavidin. Binding partner proteins are analyzed by microsequencing. Further, standard biochemical purification steps known to those skilled in the art may be used prior to microsequencing.

Yet another alternative method involves screening of peptide libraries for binding partners. Recombinant tagged or labeled MADr3 or MADr4 is used to select peptides from a peptide or phosphopeptide library which interact with MADr3 or MADr4. Sequencing of the peptides leads to identification of consensus peptide sequences which might be found in interacting proteins.

MADr3 or MADr4 binding partners identified by any of these methods or other methods, which would be known to those of ordinary skill in the art, as well as those putative binding partners discussed above, can be used in the assay method of the invention. Assaying for the presence of MADr3 or MADr4/binding partner complex is accomplished by, for example, the yeast two-hybrid system, ELISA or immunoassays using antibodies specific for the complex. In the presence of test substances which interrupt or inhibit formation of MADr3 or MADr4/binding partner interaction, a decreased amount of complex will be determined relative to a control lacking the test substance.

Assays for free MADr3 or MADr4 or binding partner are accomplished by, for example, ELISA or immunoassay using specific antibodies or by incubation of radiolabeled MADr3 or MADr4 with cells or cell membranes followed by centrifugation or filter separation steps. In the presence of test substances which interrupt or inhibit formation of MADr3 or MADr4/binding partner interaction, an increased amount of free MADr3 or MADr4 or free binding partner will be determined relative to a control lacking the test substance.

Polypeptides of the invention also can be used to assess MADr3 or MADr4 binding capacity of MADr3 or MADr4 binding molecules in cells or in cell-free preparations.

For example, malignant cells expressing a receptor for which a MAD protein of this invention is a signalling agent may be detected by using labeled MADr3 or MADr4 in a receptor binding assay, or by the use of antibodies to the receptor itself. Cells may be distinguished in accordance with the presence and density of receptors for the MAD polypeptides, thereby providing a means for predicting the susceptibility of such cells to the biological activities of the MAD polypeptides of this invention.

Agonists and Antagonists—Assays and Molecules

The MADr3 or MADr4 of the present invention may be employed in a screening process for compounds which activate (agonists) or inhibit activation (antagonists) of the MAD polypeptides of the present invention.

One method involves screening for MADr3 or MADr4 inhibitors by determining inhibition or stimulation of MADr3 or MADr4-mediated CAMP and/or adenylate cyclase accumulation. Such a method involves transfecting a eukaryotic cell with MADr3 or MADr4 to express the MADr3 or MADr4. The cell is then exposed to potential antagonists in the presence of MADr3 or MADr4. The amount of CAMP accumulation is then measured. If the potential antagonist binds the MADr3 or MADr4, and thus inhibits MADr3 or MADr4 binding, the levels of MADr3 or MADr4-mediated CAMP, or adenylate cyclase, activity will be reduced or increased.

Still another method for detecting inhibitors of MADr3 or MADr4 is the FLASHPLATE enzyme assay format of Example 5, which measures the phosphorylation reaction between the MAD polypeptide and its TGF-B receptor.

Other methods for detecting agonists or antagonists for the MADr3 or MADr4 of the present invention include the yeast based technology as described in U.S. Pat. No. 5,482,835.

Examples of potential MADr3 or MADr4 antagonists include antibodies or, in some cases, oligonucleotides which bind to the MADr3 or MADr4 but do not elicit a second messenger response such that the activity of the MADr3 or MADr4 is prevented.

Potential antagonists also include proteins which are closely related to a ligand of MADr3 or MADr4, i.e., a fragment of the ligand, which proteins have lost biological function and, when binding to MADr3 or MADr4, elicit no response.

A potential antagonist also includes an antisense construct prepared through the use of antisense technology. Antisense technology can be used to control gene expression through triple-helix formation or antisense DNA or RNA, both methods of which are based on binding of a polynucleotide to DNA or RNA.

For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix) [see, Lee et al., *Nucl. Acids Res.*, 6:3073 (1979); Cooney et al., *Science*, 241:456 (1988); and Dervan et al., *Science*, 251:1360 (1991)], thereby preventing transcription and production of the MADr3 or MADr4. The antisense RNA oligonucleotide hybridizes to the mRNA in vivo and blocks translation of the mRNA molecule into the MADr3 or MADr4 (antisense) [Okano, J. Neurochem., 56:560 (1991); and OLIGODEOXYNUCLEOTIDES AS ANTISENSE INHIBITORS OF GENE EXPRESSION, CRC Press, Boca Raton, FL (1988)]. The oligonucleotides described above can also be delivered to cells such that the antisense RNA or DNA is expressed in vivo to inhibit production of the MADr3 or MADr4.

Another potential antagonist is a small olecule which binds to MADr3 or MADr4, making it naccessible to ligands such that normal biological activity is prevented. Examples of small molecules include, but are not limited to, small peptides or peptide-like molecules. The small molecules may also bind the receptor or interaction protein to the MAD polypeptide to prevent binding. Examples of small molecules include but are not limited to small peptides or peptide-like molecules.

Potential antagonists also include fragments of the MADr3 or MADr4, which bind to the ligand and prevent the ligand from interacting with the cytoplasmic MADr3 or MADr4. MAD proteins are ubiquitous in the mammalian host and are responsible for mediating many biological functions, including many pathologies. Accordingly, it is desirous to find compounds and drugs which stimulate MADr3 or MADr4 on the one hand, and which can inhibit the function of MADr3 or MADr4 on the other hand. In general, agonists or antagonists for MADr3 or MADr4 are employed for therapeutic and prophylactic purposes for such diseases or disorders as those detailed hereinbefore, among others.

This invention additionally provides a method of treating an abnormal condition related to an excess of MADr3 or MADr4 activity which comprises administering to a subject an inhibitor compound (antagonist) as hereinabove described along with a pharmaceutically acceptable carrier in an amount effective to inhibit activation by blocking binding of ligands to the MADr3 or MADr4, or by inhibiting a second signal, and thereby alleviating the abnormal condition.

The invention also provides a method of treating abnormal conditions related to an nder-expression of MADr3 or MADr4 and its activity, hich comprises administering to a subject a herapeutically effective amount of a compound which activates the MADr3 or MADr4 polypeptide of the present invention (agonist) as described above, in combination with a pharmaceutically acceptable carrier, to thereby alleviate the abnormal condition.

The polypeptide of the present invention may be employed for characterization of receptors. The TGF-β family receptors currently includes the BMP2/BMP4, and TGFβ-1 through -3 receptors. These molecules are useful for a variety of diagnostic and therapeutic indications. The MADr3/MADr4 polypeptide is likely a signalling pathway component for one or more of these receptors as well as for yet an identified new TGFB-type receptor. Use of the MADr3/MADr4 polypeptide can assist with the identification, characterization and cloning of such receptors.

The polypeptides of the present invention may also be employed for restoration or enhancement of neurological functions diminished as a result of trauma or other damaging pathologies (such as AIDS dementia, senile dementia, etc). Accordingly, in instance where neurological functioning is diminished, an administration of a peptide of the present invention or a compound which stimulates or inhibits MADr3 or MADr4 expression may stimulate the brain and enhance proper physiological functions.

MADr3 or MADr4 may also be employed to treat ocular disorders, for example, corneal inflammation. In addition, the specificity of the TGF-β growth factors for their target cells can be exploited as a mechanism to destroy the target cell. For example, MADr3/MADr4 polypeptide can be coupled (by a wide variety of methods) to toxic molecules: for example, a radiopharmaceutical which inactivate target cells. These growth factor-toxin fusions kill the target cell (and in certain cases neighboring cells by a variety of "bystander" effects). A recent example of such toxin-fusion genes is published by Mesri, et al., J. Biol. Chem. 268:4853–62 (1993). MADr3/MADr4 polypeptides and related molecules may also be encapsulated in liposomes and may be conjugated to antibodies which recognize and bind to tumor or cell specific antigens, thereby provided a means for "targeting" cells.

In this same manner, MADr3/MADr4 polypeptide(s) can be employed as an antineoplastic compound, since members of the TGF-β family show anti-proliferative effects on transformed cells. The MADr3/MADr4 polypeptides or agonists/antagonists of same may also be employed to treat certain kidney disorders or cancers. Thus, these factors may be necessary for the proper physiological maintenance of this organ.

A significant treatment involving MADr3/MADr4 polypeptides or peptides or compounds which are agonists or antagonists thereof relates to wound healing. These compositions of the present invention may be employed for treating a wide variety of wounds including substantially all cutaneous wounds, corneal wounds, and injuries to the epithelial-lined hollow organs of the body. Wounds suitable for treatment include those resulting from trauma such as burns, abrasions and cuts, as well as from surgical procedures such as surgical incisions and skin grafting. Other conditions suitable for treatment with the polypeptides of the present invention include chronic conditions, such as chronic ulcers, diabetic ulcers, and other non-healing (trophic) conditions.

MADr3/MADr4 polypeptides may also be employed for applications related to terminal differentiation. This property can be exploited in vivo by administering the polypeptide/agonist/antagonist and inducing target cell death. This regimen is under consideration for disorders related to the hyper-proliferation of medically undesirable cell types such as cancers and other proliferative disorders (e.g. inflammation, psoriasis, etc).

Compositions and Kits

These MADr3 or MADr4 polypeptides, and compounds which activate or inhibit such MADr3 or MADr4, may be employed in combination with a suitable pharmaceutical, physiologically acceptable carrier. Such compositions comprise a therapeutically effective amount of the polypeptide or compound, and a pharmaceutically acceptable carrier or excipient. Such carriers include but are not limited to, saline, phosphate, buffered saline, dextrose, sterilized water, glycerol, ethanol, and combinations thereof. The formulation should suit the mode of administration. Selection of an appropriate carrier in accordance with the mode of administration is routinely performed by those skilled in the art.

The invention further relates to pharmaceutical packs and kits comprising one or more containers filled with one or more of the ingredients of the aforementioned compositions of the invention.

Administration

Certain disease pathologies may be partially or completely ameliorated by the systemic clinical administration of the MADr3/MADr4 polypeptides of this invention. This administration can be in the form of gene therapy (see below); or through the administration of MAD peptides agonists or antagonists synthesized from recombinant constructs of MADr3/MADr4 DNA or from peptide chemical synthesis (Woo, et al., Protein Engineering 3:29–37 (1989).

Polypeptides and other compounds of the present invention which activate or inhibit MADr3 or MADr4 may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes, among others.

The pharmaceutical compositions generally are administered in an amount effective for treatment or prophylaxis of a specific indication or indications. The amount employed of the subject polypeptide or compound will vary with the manner of administration, the employment of other active compounds, and the like, generally being in the range of about 1 μg to 100 μg. The amount of compound employed will be determined empirically, based on the response of cells in vitro and response of experimental animals to the subject polypeptides or formulations containing the subject polypeptides. In general, the compositions are administered in an amount of at least about 10 μg/kg body weight. In most cases they will be administered in an amount not in excess of about 8 mg/kg body weight per day. Preferably, in most cases, the administered dose is from about 10 μg/kg to about 1 mg/kg body weight, daily. It will be appreciated that optimum dosage will be determined by standard methods for each treatment modality and indication, taking into account the indication, its severity, route of administration, complicating conditions and the like.

Gene Therapy

The MADr3 or MADr4 polynucleotides, polypeptides, agonists and antagonists that are polypeptides may be employed in accordance with the present invention by expression of such polypeptides in treatment modalities often referred to as "gene therapy". Thus, for example, cells from a patient may be engineered with a polynucleotide, such as a DNA or RNA, to encode a polypeptide ex vivo.

The engineered cells can then be provided to a patient to be treated with the polypeptide. In this embodiment, cells may be engineered ex vivo, for example, by the use of a retroviral plasmid vector containing RNA encoding a polypeptide of the present invention. Such methods are well-known in the art and their use in the present invention will be apparent from the teachings herein.

Similarly, cells may be engineered in vivo for expression of a polypeptide in vivo by procedures known in the art. For example, a polynucleotide of the invention may be engineered for expression in a replication defective retroviral vector, as discussed above. The retroviral expression construct may then be isolated. A packaging cell is transduced with a retroviral plasmid vector containing RNA encoding a polypeptide of the present invention, such that the packaging cell now produces infectious viral particles containing the gene of interest. These producer cells may be administered to a patient for engineering cells in vivo and expression of the polypeptide in vivo. These and other methods for administering a polypeptide of the present invention should be apparent to those skilled in the art from the teachings of the present invention.

Retroviruses from which the retroviral plasmid vectors hereinabove-mentioned may be derived include, but are not limited to, Moloney Murine Leukemia Virus, Spleen Necrosis Virus, Rous Sarcoma Virus, Harvey Sarcoma Virus, Avian Leukosis Virus, Gibbon Ape Leukemia Virus, Human Immunodeficiency Virus, Adenovirus, Myeloproliferative Sarcoma Virus, and Mammary Tumor Virus. In a preferred embodiment, the retroviral plasmid vector is derived from Moloney Murine Leukemia Virus.

Such vectors will include one or more promoters for expressing the polypeptide. Suitable promoters which may be employed include, but are not limited to, the retroviral LTR; the SV40 promoter; and the human cytomegalovirus (CMV) promoter described in Miller et al., Biotechniques, 1989, 7:980–990. Cellular promoters such as eukaryotic cellular promoters including, but not limited to, the histone, RNA polymerase III, and β-actin promoters, can also be used. Additional viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention will be placed under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs herein above described); the β-actin promoter; and human growth hormone promoters. The promoter may also be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, Ψ-2, Ψ-AM, PA12, T19-14X, VT-19-17-H2, ΨCRE, Ψ(CRIP, GP+E-86, GP+envAm12, and DAN cell lines as described in Miller, A., Human Gene Therapy, 1990, 1:5–14. The vector may be transduced into the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line will generate infectious retroviral vector particles, which include the nucleic acid sequence(s) encoding the polypeptides. Such retroviral vector particles may then be employed to transduce eukaryotic cells, either in vitro or in vivo. The transduced eukaryotic cells will express the nucleic acid sequence(s) encoding the polypeptide. ukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

EXAMPLES

The present invention is further described by the following examples, which are provided solely to illustrate the invention by reference to specific embodiments. These exemplifications do not limit or circumscribe the scope of the disclosed invention.

Certain terms used herein are explained in the foregoing glossary. All examples are carried out using standard techniques, which are well known and routine to those of skill in the art, except where otherwise described in detail. Routine molecular biology techniques of the following examples can be carried out as described in standard laboratory manuals, such as Sambrook et al. All parts or amounts set out in the following examples are by weight, unless otherwise specified.

Unless otherwise stated, size separation of fragments in the examples below is carried out using standard techniques of agarose and polyacrylamide gel electrophoresis ("PAGE") as described in Sambrook et al and numerous other references, such as D. Goeddel et al., Nucleic Acids Res., 1980, 8: 4057 (i.e., using 8 percent polyacrylamide gel). Unless described otherwise, ligations are accomplished using standard buffers, incubation temperatures and times, e.g., approximately 10 units of T4 DNA ligase ("ligase") per 0.5 µg of approximately equimolar amounts of the DNA fragments to be ligated.

Example 1

Expression of MADr3 or MADr4 in Mammalian Cells

The expression plasmid, MADr3 or MADr4 HA, is made by cloning a cDNA encoding MADr3 or MADr4 into the expression vector pCDN [N. Aiyar et al, *Mol. Cell. Biochem.*, 131:75–86 (1994), incorporated by reference herein]. The selection of suitable restriction enzymes and techniques for cloning are well-known to those of skill in the art.

The expression vector pCDN contains:
(1) a human cytomegalovirus (CMV) promoter, a bovine growth hormone 3' flanking sequence, a polylinker, an SV40 intron, and a polyadenylation signal arranged so that a cDNA can be conveniently placed under expression control of the CMV promoter and operably linked to the SV40 intron and the polyadenylation signal by means of restriction sites in the polylinker;
(2) an *E. coli* origin of replication effective for propagation in E. coli and other prokaryotic cells;

(3) a bacterial neomycin phosphotransferase gene (NEO) expression cassette for geneticin (G418) selection;

(4) a murine dihydrofolate reductase (DHFR) expression cassette for methotrexate (MTX) amplification;

(5) ampicillin resistance gene for selection of plasmid-containing prokaryotic cells; and (6) an SV40 origin of replication for propagation in eukaryotic cells.

A DNA fragment encoding the entire MADr3 or MADr4 precursor is cloned into the polylinker region of the vector so that recombinant protein expression is directed by the CMV promoter. The plasmid construction strategy is as follows.

The MADr3 or MADr4 cDNA of the plasmid pMADr3 or MADr4 is amplified using primers that contain unique restriction sites. To maximize MADr3 or MADr4 expression, 5' and 3' untranslated regions (UTRs) are removed from the MADr3 or MADr4 CDNA using the unique restriction enzyme prior to insertion into the vector pCDN. Since PCR is used to trim the cDNAs, the DNA sequences are confirmed prior to expression.

Suitable primers are used in this example. The 5' primer is about 30 bp in length and contains the unique restriction site and an AUG start codon. The 3' primer, contains about 30 bp and a suitable STOP codon.

The PCR amplified DNA fragment and the vector, pCDN, are digested with the restriction enzymes unique to this sequence and then ligated. The ligation mixture is transformed into E. coli strain SURE (available from Stratagene Cloning Systems, La Jolla, Calif. 92037) the transformed culture is plated on ampicillin media plates which are then incubated to allow growth of ampicillin resistant colonies.

Plasmid DNA is isolated from resistant colonies and examined by restriction analysis and gel sizing for the presence of the MADr3 or MADr4-encoding fragment.

Human embryonic kidney 293 (HEK293) cells are selected to express the MADr3 or MADr4. For expression of recombinant MADr3 or MADr4, $2 \times 10^5$ HEK 293 cells are plated in media and incubated overnight at 37° C. in a 5% humidified incubator. The next day, 20 µg/plate of the expression vector, as described above, DNA is introduced into the cells by the calcium phosphate procedure using a mammalian transfection kit according to the manufacturer's instructions, or using DEAE-DEXTRAN, as described, for instance, in Sambrook et al.

Following transfection, the cells were incubated at 37° C. in 3% $CO_2$ for 24 hours, washed with warm Dulbecco's phosphate buffered saline (DPBS) fed with fresh media and maintained at 37° C. in 5% $CO_2$. After overnight incubation, the media is removed and replaced with fresh selection media that contains 400 µg/ml G418 to select for cells that are stably transformed with the expression vector. Selection media is replaced twice weekly for 2–4 weeks until independent cell colonies appear on the dishes. Cell colonies are individually picked and purified by limited dilution, and expanded for further analysis. The clones are grown in 6 well plates and a clonal cell line expressing human MADr3 or MADr4 is identified.

Expression is detected by Northern blot analysis. An expression product of the expected size is seen in the cell lysate, which is not seen in negative controls (HEK293 cell clones transfected with pCDN vector alone serve as negative controls).

Example 2

Bacterial Expression and Purification of the MADr3 Polypeptide

The DNA sequence encoding MADr3, ATCC # 98223 is cut from the Bluescript plasmid pHSBHI91 using EcoRI and XhoI, i.e., the restriction enzyme sites corresponding to the restriction enzyme sites on the bacterial expression vector pBluescript SK (+/−) phagemid (Stratagene, Inc.). pBluescript SK (+/−) phagemid encodes antibiotic resistance (Ampr), a bacterial origin of replication (ori), an β-galactosidase promoter operator, and other regulatory sequences [GENBANK 52325].

Plasmid GEX-t1 [Pharmacea, Uppsala, Sweden] is then digested with EcoRI and XhoI and the MADr3 sequence is ligated into the digested plasmid. MADr3 is inserted in frame with the sequence encoding for the glutathione S transferase gene in this commercially available plasmid. This plasmid is designed to generate fusion of the inserted gene, in this case MADr3, with GST. The ligation mixture is then used to transform E. coli strain SOLR (Stratagene) by conventional techniques as described in Example 2. The fusion protein MADr3-GST is purified using GST Sephadex (Pharmacea) according to manufacturer's instructions.

Example 3

Identification of Ligands or Antagonists

The expressed MADr3 or MADr4 described above in Examples 1–2 is then screened for ligands or antagonists as follows.

A. Ligand/Tissue Banks

The expressed MADr3 or MADr4 is utilized to screen compound banks, complex biological fluids, combinatorial organic and peptide libraries, etc. to identify activating ligands or antagonists. For example, the expressed MADr3 or MADr4 is employed to screen a bank of over 150 putative orphan MADr3 or MADr4 ligands, which comprises (a) naturally occurring compounds which may be putative binding proteins for MADr3 or MADr4, etc.; (b) non-mammalian, biologically active peptides for which there may be.as yet undiscovered mammalian counterparts, (c) compounds not found in nature, but which appear to activate or interact with MADr3 or MADr4 with unknown natural ligands and others.

Similarly, MADr3 or MADr4 is screened against tissue extracts of human, and other mammalian, species, such as porcine tissue. Specifically such tissue extracts include lung, liver, gut, heart, kidney, adrenals, ischemic brain, plasma, urine and placenta. Initial extraction procedures focus on removal of bulk protein via acid or ethanol precipitation to bias the separation towards peptides and small molecules that account for a high percentage of known natural ligands of MADr3 or MADr4. Subsequently milder extraction procedures are used to identify proteins. Extraction techniques employed in the formation of these tissue banks are known in the art.

B. Functional Assays

1. Xenopus Oocyte Assay.

A Xenopus oocyte system is used in the characterization of MADr3 or MADr4 because these cells accurately translate mRNA and are capable of carrying out a large number of post-translational modifications, including signal peptide cleavage, glycosylation, phosphorylation and subunit assembly. A functional assay is performed as follows:

In vitro capped RNA transcripts are prepared from linearized plasmid templates encoding the MADr3 or MADr4 cDNA with RNA polymerases using standard protocols. In vitro transcripts are suspended in water at a final concentration of 0.2 µg/ml. Ovarian lobes are removed from adult female toad; stage V defolliculated oocytes are obtained and RNA transcripts (10 ng/oocyte) are injected in a 50 nl bolus using a rummond microinjection apparatus. Two electrode voltage clamp (Warner Instruments) are used to measure he currents from individual Xenopus oocytes. Recordings are made in $Ca^{2+}$ free Barth's medium at room temperature.

2. Microphysiometer Assay

Screening of these banks is accomplished using a microphysiometer (commercially available from e.g., Molecular Devices, Ltd.). For example activation of secondary messenger systems results in the extrusion of small amounts of acid from a cell, formed largely as a result of increased metabolic activity required to fuel the intracellular signaling process. The pH changes in the media surrounding the cell are small and detectable by the microphysiometer. Thus activation of any MADr3 or MADr4 which is coupled to an energy utilizing intracellular signaling pathway may be detectable.

3. Calcium Assay

MADr3 or MADr4 stably expressed in HEK 293 cells demonstrate a robust calcium response to agonists with the appropriate rank order and potency. Basal calcium levels in the HEK 293 cells in MADr3 or MADr4-transfected or vector control cells is in the normal 100 nM to 200 nM range. HEK 293 cells expressing recombinant MADr3 or MADr4 are loaded with fura 2 and in a single day >150 selected ligands are evaluated for agonist-induced calcium mobilization. Agonists presenting a transient calcium mobilization are tested in vector control cells to determine if the calcium response was unique to the transfected MADr3 or MADr4 cells. When a unique agonist-induced response is identified, the response is reproduced in a separate group of cells and then pharmacologically characterized with concentration response curves for the effective and related ligands.

Example 4

Expression of Human MADr3 or MADr4 for Gene Therapy

Fibroblasts are obtained from a subject by skin biopsy. The resulting tissue is placed in tissue-culture medium and separated into small pieces. Small chunks of the tissue are placed on a wet surface of a tissue culture flask; approximately ten pieces are placed in each flask. The flask is turned upside down, closed tight and left at room temperature overnight. After 24 hours at room temperature, the flask is inverted; the chunks of tissue remain fixed to the bottom of the flask; and fresh media (e.g., Ham's F12 media, with 10% FBS, penicillin and streptomycin) is added. The tissue is then incubated at 37° C. for approximately one week. At this time, fresh media is added and subsequently changed every several days. After an additional two weeks in culture, a monolayer of fibroblasts emerges. The monolayer is trypsinized and scaled into larger flasks.

A vector for gene therapy (e.g., pMV-7 [Kirschmeier, P.T. et al, DNA, 7:219–25 (1988)] flanked by the long terminal repeats of the Moloney murine sarcoma virus, is digested with EcoRI and HindIII for cloning a fragment to be expression. The digested vector is treated with calf intestinal phosphatase to prevent self-ligation. The dephosphorylated, linear vector is fractionated on an agarose gel and purified, e.g., using glass beads.

MADr3 cDNA capable of expressing active MADr3 is isolated and amplified using PCR primers which correspond to the 5' and 3' end sequences, respectively. The ends of the fragment are modified, if necessary, for cloning into the vector. For instance, 5' overhanging ends may be treated with DNA polymerase to create blunt ends. 3' overhanging ends may be removed using S1 nuclease. Linkers may be ligated to blunt ends with T4 DNA ligase.

Equal quantities of the Moloney Murine Leukemia Virus linear backbone and the MADr3 or MADr4 fragment are mixed together and joined using T4 DNA ligase. The ligation mixture is used to transform E. coli and the bacteria are then plated onto agar-containing kanamycin. Kanamycin phenotype and restriction analysis confirm that the vector has the properly inserted gene.

Packaging cells (amphotropic pA317 or GP+aml2 packaging cells) are grown in tissue culture to confluent density in Dulbeccols Modified Eagles Medium (DMEM) with 10% calf serum (CS), penicillin and streptomycin. The vector containing the MADr3 gene is introduced into the packaging cells by standard techniques. Infectious viral particles containing the MADr3 or MADr4 gene are collected from the packaging cells, which now are called producer cells.

Fresh media is added to the producer cells, and after an appropriate incubation period, media is harvested from the plates of confluent producer cells. The media, containing the infectious viral particles, is filtered through a MILLIPORE filter (Bedford, Mass.) to remove detached producer cells. The filtered media is then used to infect fibroblast cells. Media is removed from a sub-confluent plate of fibroblasts and quickly replaced with the filtered media. POLYBRENE (Aldrich Chemical Co., Milwaukee, Wis.) may be included in the media to facilitate transduction. After appropriate incubation, the media is removed and replaced with fresh media. If the titer of virus is high, then virtually all fibroblasts will be infected and no selection is required. If the titer is low, then it is necessary to use a retroviral vector that has a selectable marker, such as neo or his, to select out transduced cells for expansion.

Engineered fibroblasts may then be injected into rats, either alone or after having been grown to confluence on microcarrier beads such as CYTODEX 3 beads. The injected fibroblasts produce MADr3 product, and the biological actions of the protein are conveyed to the host.

Example 5

Assay Procedures

Enzyme assay procedures for identifying agonists and antagonists of MADr3 or MADr4 include assays which use the FLASHPLATE system (DuPont), as follows. Two approaches are taken for the measurement of TGF-β receptor activity: one used the substrate, MADr3 protein, coated onto plates directly; the second utilized coating of an antibody to the substrate, MAD protein, onto the FLASHPLATE system.

A. MADr3 as Substrate Directly Coated onto FlashPlate

Initially, the phosphorylation of MAD by TGF-β receptor was optimized by varying the concentration of MAD coated onto a FlashPlate. MADr3 was dissolved in 0.1 M sodium bicarbonate buffer (pH 9.6) and added to FlashPlate wells in 100 µL aliquots containing 100–1000 ng of protein. After an overnight incubation at room temperature, each well was washed 2×with 200 µL of the coating buffer. The plate was air dried and used either immediately or stored at 4° C. Plates are viable for 2–3 weeks when stored at 4° C. For he phosphorylation reaction, each well received a total volume of 90 µL containing 33 mM Tris-HCl (pH 7.4), 17 mM $MgCl_2$, 33 µM ATP, 0.7 mM DTT, 0.25 µCi of $[g^{33}P]$-ATP (DuPont NEG-302H), and 0.3 units of TGF-β receptor. Background counts were measured by not adding any receptor. The plate was incubated at 30° C. for 3 hours. The solution was aspirated and the wells were rinsed 1× with 250 µL of 10 mM sodium pyrophosphate/PBS to terminate the reaction. The plate was counted on a Packard TopCount.

In addition, TGF-β receptor was titrated (0.00–0.08 units) to determine the level of enzyme required to obtain a detectable phosphorylation reaction on a FlashPlate coated with a set amount of MADr3 (750 ng/well). Reaction conditions were as above except that the plate was incubated overnight at 30° C.

B. Antibody to MADr3 Coated onto FlashPlate

FlashPlate was coated with 100 μL per well of an antibody against MADr3 at a concentration of 5 μg/mL in PBS. After an overnight incubation at room temperature, the plate was washed twice with PBS and then blocked with 1% BSA/PBS for at least 2 hours at room temperature. The plate was air dried and stored at 4° C. until use. Plates are viable for 2–3 weeks when stored at 4° C.

The phosphorylation reaction was performed in the plate using a total volume of 60 μL per well containing 33 mM Tris-HCl (pH 7.4), 17 MM $MgCl_2$, 33 μM ATP, 0.7 mM DTT, 0.25 μCi of $[\gamma^{33}P]$-ATP (DuPont NEG-302H), 20 μg of MADr3 and varying amounts of recombinant TGF-β receptor. To determine non-specific binding (NSB), MADr3 was omitted from the reaction. The plate was incubated overnight at 30° C. Following aspiration of the solution, the wells were rinsed 1x with 250 μL per well of 10 mM sodium pyrophosphate/PBS which reduces non-specific binding. The plate was counted on a Packard TopCount.

The MAD protein immobilized directly onto FlashPlate serves as a functional substrate for TGF-β receptor. The reaction only required a single pyrophosphate rinse to remove unreacted $[\gamma^{33}P]$-ATP and receptor from the wells. Background counts in wells containing no receptor was about 100 cpm after the rinse yielding a signal to noise ratio of $\geq 10$. This ratio increases as the amount of MADr3 coated on the plate increases. Immobilized MADr3 substrate at 750 ng/well can be phosphorylated in a dose dependent fashion, thus allowing quantitation of TGF-β receptor activity. The signal to noise ratio at 0.01 units of TGF-β receptor was 50:1, indicating that the detection limit was considerably lower than the levels tested here.

Coating the plate with an antibody against the MADr3 substrate is also efficient in enabling the bound substrate to be phosphorylated by TGF-β receptor. The reaction is dose dependent with respect to the amount of receptor added. As configured, the coated plate captured both phosphorylated as well as unphosphorylated substrate as the antisera was not specific for either form.

Various options are available for formatting an enzyme assay. Such assays enable one to insert into the system an unknown compound, which can inhibit the phosphorylation reaction by interacting with the MAD polypeptide or with the receptor. The choice of format depends upon the sensitivity required and the purpose of the assay: whether it is designed to quantitate enzyme levels or to measure inhibition in kinetic studies. Regardless of format, such enzyme assays are advantageous both for automation and for high throughput screening.

It will be clear that the invention may be practiced otherwise than as particularly described in the foregoing description and examples. Numerous modifications and variations of the present invention are possible in light of the above teachings and, therefore, are within the scope of the appended claims.

---

What is claimed is:

1. A process for producing a polypeptide comprising expressing, from a host cell comprising a vector comprising a polynucleotide encoding the amino acid sequence as set forth in SEQ ID NO:2, a polypeptide encoded by said polynucleotide.

2. An isolated polypeptide comprising an amino acid sequence as set forth in SEQ ID NO: 2.

3. The isolated polypeptide of claim 2 consisting of the amino acid sequence of SEQ ID NO:2.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 2333 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

```
GGCACGAGGT CGAGCCCAGC CCCGCCGGGG GCGCTCCTCG CCGCCCGCGC GCCCTCCCCA        60

GCCATGTCGT CCATCCTGCC TTTCACTCCC CCGATCGTGA AGCGCCTGCT GGGCTGGAAG       120

AAGGGCGAGC AGAACGGGCA GGAGGAGAAA TGGTGCGAGA AGGCGGTCAA GAGCCTGGTC       180

AAGAAACTCA AGAAGACGGG GCAGCTGGAC GAGCTGGAGA AGGCCATCAC CACGCAGAAC       240

GCCAACACCA AGTGCATCAC CATCCCCAGG TCCCTGGATG GCCGGTTGCA GGTGTCCCAT       300

CGGAAGGGGC TCCCTCATGT CATCTACTGC CGCCTGTGGC GATGGCCAGA CCTGCACAGC       360

CACCACGAGC TGCGGGCCAT GGAGCTGTGT GAGTTCGCCT TCAATATGAA GAAGGACGAG       420

GTCTGCGTGA ATCCCTACCA CTACCAGAGA GTAGAGACAC CAGTTCTACC TCCTGTGTTG       480

GTGCCACGCC ACACAGAGAT CCCGGCCGAG TTCCCCCCAC TGGACGACTA CAGCCATTCC       540

ATCCCCGAAA ACACTAACTT CCCCGCAGGC ATCGAGCCCC AGAGCAATAT TCCAGAGACC       600
```

-continued

```
CCACCCCCTG GCTACCTGAG TGAAGATGGA GAAACCAGTG ACCACCAGAT GAACCACAGC      660

ATGGACGCAG GTTCTCCAAA CCTATCCCCG AATCCGATGT CCCCAGCACA TAATAACTTG      720

GACCTGCAGC CAGTTACCTA CTGCGAGCCG GCCTTCTGGT GCTCCATCTC CTACTACGAG      780

CTGAACCAGC GCGTCGGGGA GACATTCCAC GCCTCGCAGC CATCCATGAC TGTGGATGGC      840

TTCACCGACC CCTCCAATTC GGAGCGCTTC TGCCTAGGGC TGCTCTCCAA TGTCAACAGG      900

AATGCAGCAG TGGAGCTGAC ACGGAGACAC ATCGGAAGAG GCGTGCGGCT CTACTACATC      960

GGAGGGGAGG TCTTCGCAGA GTGCCTCAGT GACAGCGCTA TTTTTGTCCA GTCTCCCAAC     1020

TGTAACCAGC GCTATGGCTG GCACCCGGCC ACCGTCTGCA AGATCCCACC AGGATGCAAC     1080

CTGAAGATCT TCAACAACCA GGAGTTCGCT GCCCTCCTGG CCCAGTCGGT CAACCAGGGC     1140

TTTGAGGCTG TCTACCAGTT GACCCGAATG TGCACCATCC GCATGAGCTT CGTCAAAGGC     1200

TGGGGAGCGG AGTACAGGAG ACAGACTGTG ACCAGTACCC CCTGCTGGAT TGAGCTGCAC     1260

CTGAATGGGC CTTTGCAGTG GCTTGACAAG GTCCTCACCC AGATGGGCTC CCCAAGCATC     1320

CGCTGTTCCA GTGTGTCTTA GAGACATCAA GTATGGTAGG GGAGGGCAGG CTTGGGGAAA     1380

ATGGCCATGC AGGAGGTGGA GAAAATTGGA ACTCTACTCA ACCCATTGTT GTCAAGGAAG     1440

AAGAAATCTT TCTCCCTCAA CTGAAGGGGT GCACCCACCT GTTTTCTGAA ACACACGAGC     1500

AAACCCAGAG GTGGATGTTA TGAACAGCTG TGTCTGCCAA ACACATTTAC CCTTTGGCCC     1560

CACTTTGAAG GGCAAGAAAT GGCGTCTGCT CTGGTGGCTT AAGTGAGCAG AACAGGTAGT     1620

ATTACACCAC CGGCCCCCTC CCCCCAGATC TTTTTTTGAG TGACAGCTTT CTGGGATGTC     1680

ACAGTCCAAC CAGAAACACC CCTCTGTCTA GGACTGCAGT GTGGAGTTCA CCTTGGAAGG     1740

GCGTTCTAGG TAGGAAGAGC CCGCAGGGCC ATGCAGACCT CATGCCCAGC TCTCTGACGC     1800

TTGTGACAGT GCCTCTTCCA GTGAACATTC CCAGCCCAGC CCCGCCCCGC CCCGCCCCAC     1860

CACTCCAGCA GACCTTGCCC CTTGTGAGCT GGATAGACTT GGGATGGGGA GGGAGGGAGT     1920

TTTGTCTGTC TCCCTCCCCT CTCAGAACAT ACTGATTGGG AGGTGCGTGT TCAGCAGAAC     1980

CTGCACACAG GACAGCGGGA AAAATCGATG AGCGCCACCT CTTTAAAAAC TCACTTACGT     2040

TTGTCCTTTT TCACTTTGAA AAGTTGGAAG GATCTGCTGA GGCCCAGTGC ATATGCAATG     2100

TATAGTGTCT ATTATCACAT TAATCTCAAA GAGATTCGAA TGACGGTAAG TGTTCTCATG     2160

AAGCAGGAGG CCCTTGTCGT GGGATGGCAT TTGGTCTCAG GCAGCACCAC ACTGGGTGCG     2220

TCTCCAGTCA TCTGTAAGAG CTTGCTCCAG ATTCTGATGC ATACGGCTAT ATTGGTTTAT     2280

GTAGTCAGTT GCATTCATTA AATCAACTTT ATCATAAAAA AAAAAAAAA AAA             2333
```

(2) INFORMATION FOR SEQ ID NO:2:

(i) SEQUENCE CHARACTERISTICS:
        (A) LENGTH: 425 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Ser Ser Ile Leu Pro Phe Thr Pro Pro Ile Val Lys Arg Leu Leu
 1               5                  10                  15

Gly Trp Lys Lys Gly Glu Gln Asn Gly Gln Glu Glu Lys Trp Cys Glu
            20                  25                  30

Lys Ala Val Lys Ser Leu Val Lys Lys Leu Lys Lys Thr Gly Gln Leu
```

```
            35                  40                  45
Asp Glu Leu Glu Lys Ala Ile Thr Thr Gln Asn Ala Asn Thr Lys Cys
     50                  55                  60

Ile Thr Ile Pro Arg Ser Leu Asp Gly Arg Leu Gln Val Ser His Arg
 65                  70                  75                  80

Lys Gly Leu Pro His Val Ile Tyr Cys Arg Leu Trp Arg Trp Pro Asp
                     85                  90                  95

Leu His Ser His His Glu Leu Arg Ala Met Glu Leu Cys Glu Phe Ala
                100                 105                 110

Phe Asn Met Lys Lys Asp Glu Val Cys Val Asn Pro Tyr His Tyr Gln
            115                 120                 125

Arg Val Glu Thr Pro Val Leu Pro Pro Val Leu Val Pro Arg His Thr
       130                 135                 140

Glu Ile Pro Ala Glu Phe Pro Pro Leu Asp Asp Tyr Ser His Ser Ile
145                 150                 155                 160

Pro Glu Asn Thr Asn Phe Pro Ala Gly Ile Glu Pro Gln Ser Asn Ile
                165                 170                 175

Pro Glu Thr Pro Pro Pro Gly Tyr Leu Ser Glu Asp Gly Glu Thr Ser
            180                 185                 190

Asp His Gln Met Asn His Ser Met Asp Ala Gly Ser Pro Asn Leu Ser
       195                 200                 205

Pro Asn Pro Met Ser Pro Ala His Asn Asn Leu Asp Leu Gln Pro Val
210                 215                 220

Thr Tyr Cys Glu Pro Ala Phe Trp Cys Ser Ile Ser Tyr Tyr Glu Leu
225                 230                 235                 240

Asn Gln Arg Val Gly Glu Thr Phe His Ala Ser Gln Pro Ser Met Thr
                245                 250                 255

Val Asp Gly Phe Thr Asp Pro Ser Asn Ser Glu Arg Phe Cys Leu Gly
            260                 265                 270

Leu Leu Ser Asn Val Asn Arg Asn Ala Ala Val Glu Leu Thr Arg Arg
       275                 280                 285

His Ile Gly Arg Gly Val Arg Leu Tyr Tyr Ile Gly Gly Glu Val Phe
290                 295                 300

Ala Glu Cys Leu Ser Asp Ser Ala Ile Phe Val Gln Ser Pro Asn Cys
305                 310                 315                 320

Asn Gln Arg Tyr Gly Trp His Pro Ala Thr Val Cys Lys Ile Pro Pro
                325                 330                 335

Gly Cys Asn Leu Lys Ile Phe Asn Asn Gln Glu Phe Ala Ala Leu Leu
            340                 345                 350

Ala Gln Ser Val Asn Gln Gly Phe Glu Ala Val Tyr Gln Leu Thr Arg
       355                 360                 365

Met Cys Thr Ile Arg Met Ser Phe Val Lys Gly Trp Gly Ala Glu Tyr
370                 375                 380

Arg Arg Gln Thr Val Thr Ser Thr Pro Cys Trp Ile Glu Leu His Leu
385                 390                 395                 400

Asn Gly Pro Leu Gln Trp Leu Asp Lys Val Leu Thr Gln Met Gly Ser
                405                 410                 415

Pro Ser Ile Arg Cys Ser Ser Val Ser
            420                 425
```

(2) INFORMATION FOR SEQ ID NO:3:

(i) SEQUENCE CHARACTERISTICS:
    (A) LENGTH: 277 base pairs (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:3:

```
CTGGCTCAGT CTNTTAATCA GGGTNTTGAA GCAGTCTATC ANCTAACTAG AATGGGGGGG      60

ATAAGTTTTT TGTTTNGTGA AAGGGTGNGG AGCAGTATAC CGAAGTCAGT ACGNTAACAN     120

NAGACTNCTA ACTGGATTGA ACTTCATNTG AATGGACCTC TACANTGGNT GGACAAAGTA    180

TTAACTCAGA TNGGATACCC TNCAGTGCGT TGCTCAAGNA TGTCATAAAG CTTCACCAAT    240

CAAGTCCCAT GAAAAAGACT TAAANGTAAC AACTCTN                             277
```

(2) INFORMATION FOR SEQ ID NO:4:

(i) SEQUENCE CHARACTERISTICS:
        (A) LENGTH: 189 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

```
TGACATACTG CATGCCTGAG TGAGAGACGA TCCGAACTCT GTGCTAGTCA TCTGCAGCAC      60

ACTAACTATT ATGCTGATGT GACTCATTGC AGTTTAAACA TTTCTTCTGT TTGCATCTCT    120

AGTAGAAATG GAAAATAACC ACTCCCTGGC GCTCTTTTCA TTAAATTTTC ATATTTTTGA    180

AAAAAAAAA                                                             189
```